(12) United States Patent
Flentov et al.

(10) Patent No.: US 7,949,488 B2
(45) Date of Patent: May 24, 2011

(54) MOVEMENT MONITORING SYSTEMS AND ASSOCIATED METHODS

(75) Inventors: Peter Flentov, Carlisle, MA (US);
Dennis M. Darcy, Dracut, MA (US);
Curtis A. Vock, Boulder, CO (US)

(73) Assignee: Nike, Inc., Beaverton, OR (US)

( * ) Notice: Subject to any disclaimer, the term of this patent is extended or adjusted under 35 U.S.C. 154(b) by 0 days.

(21) Appl. No.: 11/243,945

(22) Filed: Oct. 5, 2005

(65) Prior Publication Data

US 2006/0031039 A1 Feb. 9, 2006

Related U.S. Application Data

(63) Continuation of application No. 10/289,039, filed on Nov. 6, 2002, now Pat. No. 6,963,818, which is a continuation of application No. 09/784,783, filed on Feb. 15, 2001, now Pat. No. 6,516,284, which is a continuation of application No. 09/353,530, filed on Jul. 14, 1999, now Pat. No. 6,496,787, which is a continuation of application No. 08/764,758, filed on Dec. 12, 1996, now Pat. No. 5,960,380, which is a continuation of application No. 08/344,485, filed on Nov. 21, 1994, now Pat. No. 5,636,146.

(51) Int. Cl.
*G01P 15/00* (2006.01)

(52) U.S. Cl. ............ 702/141; 702/33; 702/75; 702/81; 702/96; 701/3; 701/7; 701/70; 368/10; 368/11; 368/14; 346/33 R; 73/488; 73/489

(58) Field of Classification Search ............... 702/33, 702/75–77, 81, 96–98, 141–143; 73/488, 73/489; 368/10, 11, 14; 701/3, 7, 70; 346/33 R
See application file for complete search history.

(56) References Cited

U.S. PATENT DOCUMENTS

| | | | | |
|---|---|---|---|---|
| 3,788,647 A | * | 1/1974 | Evans | 473/223 |
| 4,089,057 A | * | 5/1978 | Eriksson | 702/158 |
| 4,220,996 A | * | 9/1980 | Searcy | 702/160 |
| 4,223,211 A | | 9/1980 | Allsen et al. | |
| 4,371,945 A | * | 2/1983 | Karr et al. | 702/160 |
| 4,402,147 A | | 9/1983 | Wu | |
| 4,510,704 A | | 4/1985 | Johnson | |
| 4,578,769 A | | 3/1986 | Frederick | |
| 4,694,694 A | * | 9/1987 | Vlakancic et al. | 73/386 |

(Continued)

FOREIGN PATENT DOCUMENTS

GB 2137363 10/1984

OTHER PUBLICATIONS

Bedi, 'A Simplified Optical Arrangement for the Laser Doppler Velocimeter', Oct. 1970, UOS Publication, vol. 4, pp. 27-28.*

(Continued)

*Primary Examiner* — Mohamed Charioui
*Assistant Examiner* — Elias Desta
(74) *Attorney, Agent, or Firm* — Banner & Witcoff Ltd.

(57) ABSTRACT

Systems and methods are disclosed that monitor movement of a person, or of a vehicle ridden by the person, to determine speed, distance traveled and/or airtime of the person or vehicle. Accelerometer-based sensors, pressure sensors or Doppler sensors may be employed in these systems and methods. A liquid crystal display may attach to the person to display speed, distance traveled and/or airtime.

16 Claims, 16 Drawing Sheets

U.S. PATENT DOCUMENTS

| | | | |
|---|---|---|---|
| 4,699,379 A | | 10/1987 | Chateau et al. |
| 4,703,445 A | | 10/1987 | Dassler |
| 4,736,312 A | | 4/1988 | Dassler et al. |
| 4,757,714 A | * | 7/1988 | Purdy et al. .................. 73/597 |
| 4,759,219 A | | 7/1988 | Cobb et al. |
| 4,763,287 A | | 8/1988 | Gerhaeuser et al. |
| 4,771,394 A | | 9/1988 | Cavanagh |
| 4,821,218 A | * | 4/1989 | Potsch ...................... 73/514.01 |
| 4,824,107 A | | 4/1989 | French |
| 4,883,271 A | | 11/1989 | French |
| 4,956,628 A | | 9/1990 | Furlong |
| 4,991,126 A | * | 2/1991 | Reiter ........................ 702/152 |
| 5,033,013 A | | 7/1991 | Kato et al. |
| 5,148,002 A | | 9/1992 | Kuo et al. |
| 5,191,792 A | * | 3/1993 | Gloor ........................ 73/178 R |
| 5,343,445 A | * | 8/1994 | Cherdak ...................... 368/10 |
| 5,446,775 A | | 8/1995 | Wright et al. |
| 5,452,269 A | | 9/1995 | Cherdak |
| 5,471,405 A | | 11/1995 | Marsh |
| 5,485,402 A | | 1/1996 | Smith et al. |
| 5,500,635 A | | 3/1996 | Mott |
| 5,513,854 A | | 5/1996 | Daver |
| 5,524,637 A | | 6/1996 | Erickson |
| 5,526,290 A | * | 6/1996 | Kanzaki ...................... 702/160 |
| 5,724,265 A | | 3/1998 | Hutchings |
| 5,925,001 A | | 7/1999 | Hoyt et al. |
| 5,955,667 A | | 9/1999 | Fyfe |
| 6,305,221 B1 | | 10/2001 | Hutchings |

OTHER PUBLICATIONS

Complaint, Civil Action 08-CV-01447 MSK-BNB, Jul. 26, 2006.
First Amended Complaint, Civil Action 08-CV-01447 MSK-BNB, Aug. 16, 2006.
Answer, Affirmative Defenses, Counterclaims And Demand For Jury Trial, Civil Action 06-CV-01447 MSK-BNB, Oct. 9, 2006.
Complaint Civil Action 05-CV-02323, Nov. 16, 2005.
Complaint, Civil Action 06-CV-01100-WDM-PAC, Jun. 8, 2006.
Defendants Polar Electro Inc.'s And Polar Eloclro Oy's Answer And Affirmative Defenses; Polar Electro Inc.'s Counterclaim and Demand For Jury Trial, Civil Action 06-CV-01100-WDM-PAC, Jun. 29, 2006.
Nobbe, "Olympic Athletes Get a Boost from Technology," Machine Design, Aug. 25, 1988.

* cited by examiner

MOVEMENT MONITORING SYSTEMS AND ASSOCIATED METHODS

RELATED APPLICATIONS

This application is a continuation of U.S. application Ser. No. 10/289,039 filed Nov. 6, 2002, now U.S. Pat. No. 6,963,818 which is a continuation of U.S. application Ser. No. 09/784,783 filed Feb. 15, 2001, now U.S. Pat. No. 6,516,284 which is a continuation of U.S. Ser. No. 09/353,530, filed Jul. 14, 1999, now U.S. Pat. No. 6,496,787 which is a continuation of U.S. Ser. No. 08/764,758 (now U.S. Pat. No. 5,960,380), filed Dec. 12, 1996, which is a continuation of U.S. Ser. No. 08/344,485 (now U.S. Pat. No. 5,636,146), filed Nov. 21, 1994, each of which are incorporated herein by reference.

FIELD OF THE INVENTION

The invention relates generally to the measurement of the loft time and speed. Such measurements are particularly useful in sporting activities where users desire information relating to their speed and/or loft, or "air" time.

BACKGROUND OF THE INVENTION

It is well known that many skiers enjoy high speeds and jumping motions while traveling down the slope. High speeds refer to the greater and greater velocities which skiers attempt in navigating the slope successfully (and sometimes unsuccessfully). The jumping motions, on the other hand, include movements which loft the skier into the air. Generally, the greater the skier's speed, the higher the skier's loft into the air.

The interest in high speed skiing is apparent simply by observing the velocity of skiers descending the mountain. The interest in the loft motion is less apparent; although it is known that certain enthusiastic skiers regularly exclaim "let's catch some air" and other assorted remarks when referring to the amount and altitude of the lofting motion.

The sensations of speed and jumping are also readily achieved in other sporting activities, such as in mountain biking. Many mountain bikers, like the aforementioned skiers, also crave greater speeds and "air" time.

However, persons in such sporting activities typically only have a qualitative sense as to speed and loft or "air" time. For example, a typical snowboarding person might regularly exclaim after a jump that she "caught" some "big sky," "big air" or "phat air" without ever quantitatively knowing how much time really elapsed in the air.

It is, accordingly, an object of the invention to provide apparatus and methods for determining the "air" time of participants in sporting activities such as skiing and mountain biking.

It is another object of the invention to provide apparatus and methods for determining the speed of participants in sporting activities such as skiing and mountain biking.

It is yet another object of the invention to provide improvements to sporting devices which are ridden by sporting participants, and which provide a determination of speed and/or loft time of the device.

These and other objects of the invention will become apparent in the description which follows.

SUMMARY OF THE INVENTION

The invention concerns the detection and display of loft, or "air" time and/or speed of vehicles such as sporting vehicles, including skis, bikes, and snowboards. The invention thus provides a visual and quantitative measure of how much "air" time and, in certain aspects, how fast a user moves in a particular activity.

The invention provides, in one aspect, apparatus for determining the loft time of a moving vehicle off of a surface. A loft sensor senses a first condition that is indicative of the vehicle leaving the surface, and further senses a second condition indicative of the vehicle returning to the surface. A microprocessor subsystem, e.g., a microcontroller, determines a loft time that is based upon the first and second conditions, and the loft time is thereafter displayed to a user of the apparatus by a display, e.g., a LCD or LED display. Preferably, a power module such as a battery is included in the apparatus to power the several components. In addition, a housing preferably connects and protects the microprocessor subsystem and the user interface; and further such that the housing is attachable to the vehicle.

According to another aspect, the invention includes memory for storing information representative of at least one of the following: (i) the first and second conditions, (ii) the loft time, (iii) a speed of the vehicle, (iv) successive records of loft time, (v) an average loft time, (vi) a total loft time, (vii) a dead time, (viii) a real activity time, and (ix) a numerical ranking of successive records.

One preferred aspect of the invention includes a speed sensor, connected to the microprocessor subsystem, which senses a third condition that is indicative of a velocity of the vehicle. In this aspect, the microprocessor subsystem includes means for converting the third condition to information representative of a speed of the vehicle. Accordingly, the apparatus provides a user with both loft time, e.g., "air" time, and a speed of the vehicle.

In yet another aspect, the display of the invention can display selective information, including one or more of the following: the loft time; a speed of the vehicle; a peak loft time; an average loft time; a total loft time; a dead time; a real activity time; an average speed; an indication that loft time is being displayed; an indication that speed is being displayed; an indication that dead time is being displayed; an indication that real activity time is being displayed; successive records of loft information; successive records of speed information; a distance traveled by the vehicle; a height achieved by the vehicle off of the surface; and an indication of a number of a successive record relative to all successive records.

In still another aspect, the invention includes a user interface for providing external inputs to the apparatus, including one or more of the following: a start/stop button for selectively starting and stopping the acquisition of data by the apparatus; a display-operate button for activating the display means selectively; a speed/loft toggle button for alternatively commanding a display of loft time information and speed information of the vehicle; means for commanding a display of successive records of loft time information selectively; means for commanding a display of successive records of speed information selectively; means for commanding a display of information corresponding to average loft time; means for commanding a display of information corresponding to average speed; means for commanding a display of total loft time; means for commanding a display of dead time; means for commanding a display of distance traveled by the vehicle; means for commanding a display of height achieved by the vehicle off of the surface; and means for commanding a display of real activity time.

Preferably, the microprocessor subsystem of the invention includes a clock element, e.g., a 24-hour clock, for providing information convertible to an elapsed time. Accordingly, the subsystem can perform various calculations, e.g., dead time, on the data acquired by the apparatus for display to a user.

In another aspect, the loft sensor is constructed with one of the following technologies: (i) an accelerometer that senses a vibrational spectrum; (ii) a microphone assembly that senses a noise spectrum; (iii) a switch that is responsive to a weight of a user of the vehicle; (iv) a voltage-resistance sensor that generates a voltage indicative of a speed of the vehicle; and (v) a plurality of accelerometers connected for evaluating a speed of the vehicle.

In a preferred aspect, the loft sensor of the invention senses a spectrum of information, e.g., a vibrational or sound spectrum, and the microprocessor subsystem determines the first and second conditions relative to a change in the spectrum of information. Further, the microprocessor subassembly interprets the change in the spectrum to determine the loft time.

For example, one aspect of a loft sensor according to the invention includes one or more accelerometers that generate a vibrational spectrum of the vehicle. In such an aspect, the first and second conditions correspond to a change in the vibrational spectrum. By way of another example, one loft sensor of the invention includes a microphone subassembly that generates a noise spectrum of the vehicle; and, in this aspect, the first and second conditions correspond to a change in the detected noise spectrum. Because these spectrums are influenced by the particular activity of a user, e.g., standing in a ski line, a microprocessor subsystem of the invention preferably includes means for assessing boundary conditions of the spectrum and for excluding certain conditions from the determination of loft time. Accordingly, if a skier is in a lift line, such conditions are effectively ignored. One boundary condition, therefore, according to an aspect of the invention, includes an elapsed time between the first condition and the second condition that is less than approximately 500 ms; such that events that are within this boundary condition are excluded from the determination of loft time. One other boundary condition, in another aspect, includes an elapsed time between the first condition and the second condition that is greater than approximately five seconds; such that events that are outside this boundary condition are excluded from the determination of loft time. Because these boundary conditions are important in the aspects of the invention which utilize a spectrum of information, the apparatus preferably utilizes a user interface for providing selective external inputs to the microprocessor subsystem and for adjusting the boundary conditions selectively.

In still another aspect of the invention, the microprocessor subassembly includes means for determining a pitch of the spectrum by determining a best-fit sine wave to a primary frequency of at least part of the spectrum and means for correlating the pitch to a vehicle speed. Accordingly, the invention can detect spectrum information and correlate that information to a speed of the vehicle. Typically, a higher pitch frequency corresponds to a higher vehicle speed and a lower pitch frequency corresponds to a lower vehicle speed. However, in another aspect, the selected pitch frequency can be calibrated relative to a selected vehicle and speed.

The invention also provides, in another aspect, means for storing information including look-up tables with pitch-to-speed conversions for a plurality of vehicles. This is useful because different vehicles have different associated noise and/or sound spectrums associated with the vehicle. Accordingly, the invention in this aspect includes memory for storing the respective calibration information of the different vehicles (typically in a look-up table format) so that a user can utilize the invention on different vehicles and still determine speed accurately. Specifically, a particular pitch is associated with a particular speed for a particular vehicle; and that association is selectively made by the user.

The vehicles which are preferably used, according to the invention, include (i) a snowboards, (ii) snow skis, (iii) water skis, (iv) skis for ski jumping, and (v) skis for ski flying. However, in certain aspects of the invention, a human vehicle can be used; although the processing power required to accurately process speed and/or loft information in this aspect is significantly increased.

In several aspects of the invention, the microprocessor subassembly includes one or more of the following: means for selectively starting and stopping the acquisition of data by the apparatus; means for responding to an external request to activate the display means; means for responding to an external request to alternatively display the loft time and a speed of the vehicle; means for calculating a speed of the vehicle; means for responding to an external request to display successive records of loft time information; means for responding to an external request to display successive records of speed information; means for determining an average speed; means for determining a total loft time; means for determining a dead time; means for responding to an external request to display information corresponding to an average loft time; means for responding to an external request to display information corresponding to an average speed; means for responding to an external request to display a total loft time; means for responding to an external request to display a dead time; means for responding to an external request to display a distance traveled by the vehicle; means for responding to an external request to display a height achieved by the vehicle off of the surface; and means for responding to an external request to display a real activity time.

The invention also provides certain improvements to sporting vehicles of the type ridden by a user on a surface (e.g., sporting vehicle such as (i) snowboards, (ii) snow skis, (iii) water skis, (iv) skis for ski jumping, and (v) skis for ski flying). The improvements include, in one aspect, a speed sensor having (i) a voltage-measuring circuit including a pair of conductors arranged to contact the surface so that the surface is part of the circuit, and (ii) an electromagnet for selectively generating a magnetic field on the circuit, wherein a voltage generated by the circuit is proportional to a speed of the vehicle. In such an aspect, the microprocessor subsystem determines a speed of the vehicle that is based upon the voltage, and that speed is displayed to a user.

The invention also provides certain methodologies. For example, in one aspect, the invention provides a method for determining the loft time of a moving vehicle off of a surface, comprising the steps of: (1) sensing the vehicle leaving the surface at a first time; (2) sensing the vehicle returning to the surface at a second time; (3) determining a loft time from the first and second times, and (4) displaying the loft time to a user of the apparatus.

The invention is next described further in connection with preferred embodiments, and it will be apparent that various additions, subtractions, and modifications can be made by those skilled in the art without departing from the scope of the invention.

BRIEF DESCRIPTION OF THE DRAWINGS

A more complete understanding of the invention may be obtained by reference to the drawings, in which.

DETAILED DESCRIPTION OF ILLUSTRATED EMBODIMENTS

Figure 1:
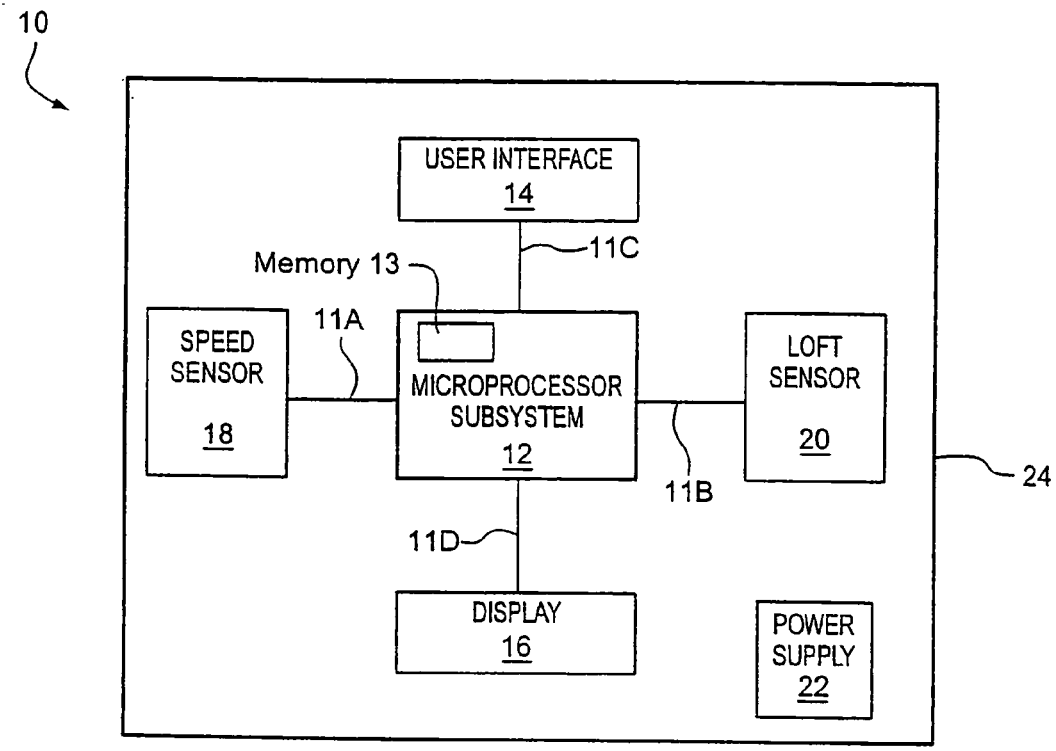
FIG. 1 illustrates a system constructed according to the invention for determining loft and speed of a sporting vehicle carrying the system.

FIG. 1 illustrates a system 10 constructed according to the invention. A microprocessor subsystem 12 controls the system 10 and connects to a user interface 14, a display 16, speed sensor 18 and loft sensor 20. A power supply 22, e.g., a battery, provides power to the system 10 and connects to the components 12, 14, 16, 18 and 20 via appropriate electrical interconnections (not shown). The microprocessor subsystem 12 includes memory 13 for storing data acquired by the system 10.

The system 10 is incorporated into a relatively small housing, shown by the outline 24. The housing 24 is preferably arranged to protect the components 12, 14, 16, 18 and 20 from the elements of nature—such as rain, snow, sand and dust, each of which is expected during the ordinary course of usage on a ski slope and/or mountain bike trail. In addition, the housing 24 is attachable to a vehicle, such as a ski or mountain bike, by means such as a glue or a mechanical mount, e.g., screws. Alternatively, the housing (and hence the system 10) is incorporated integrally with the vehicle, such as inside a ski, such that only the display 16 and user interface 14 are visible and accessible.

Briefly, the invention shown in FIG. 1 operates as follows. The housing 24 is attached or mounted to a sporting device, such as a ski or mountain bike, such that a user of the ski or mountain bike can access the system 10. During motion of the ski or mountain bike, the speed sensor 18 sends velocity information (over communication line 11a) to the microprocessor subsystem 12; while the loft sensor 20 sends loft or "air" time information (over communication line 11b) to the microprocessor subsystem 12. The speed information and loft time information are processed by the microprocessor subsystem 12 to quantify actual speed, e.g., in miles per hour, and actual loft time, e.g., in seconds. The actual speed and loft time are thereafter stored in internal memory 13 until, at least, the speed and time data are accessed by a user of the system 10. Upon access through the user interface 14 (communicating with the microprocessor subsystem 12 via communication line 11c), a user of the system 10 can command the display of the speed and loft time data (sent across communication line 11d) on the display 16 in order to evaluate his or her performance in the sporting activity.

In an alternative embodiment, the speed and loft information can be stored prior to processing by the microprocessor subsystem 12; and later post-processed for display on the display 16 when commanded by a user of the system 10. Such an embodiment may be useful to conserve energy and to perform calculations to quantify the speed and loft data in a "batch" mode, such as known to those skilled in the art.

The system 10 of FIG. 1 preferably includes both of the speed sensor 18 and loft sensor 20; although it is not necessary for both sensors to be present in accord with the invention. Rather, in certain embodiments of the invention, only the loft sensor 20 is present within the system 10; and in certain other embodiments of the invention, only the speed sensor 18 is present within the system 10. Accordingly, in these embodiments, only the loft data or speed data, respectively, are available to a user of the system because the sensor which measures the information is absent.

Figure 2:
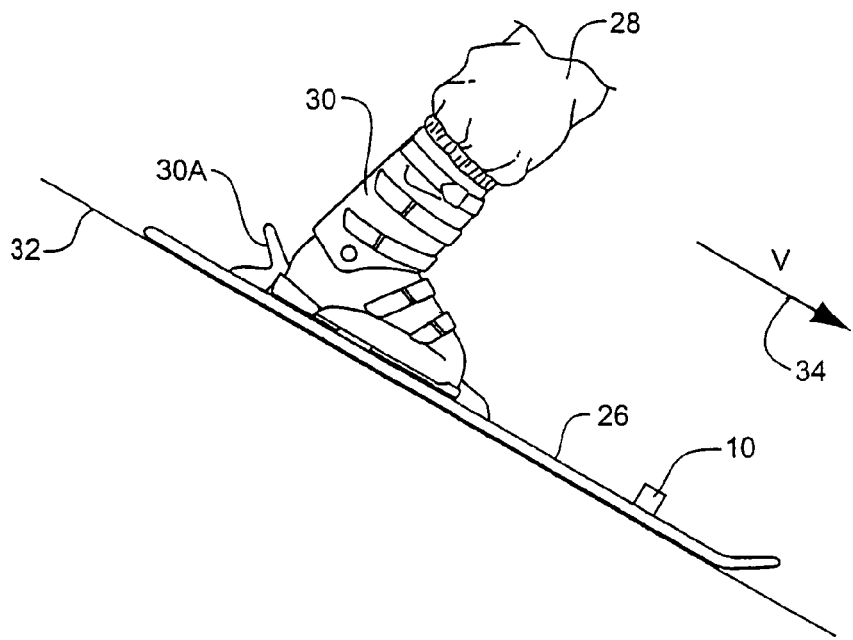
FIGS. 2, 2A and 2B show illustrative uses for the system 10 shown in FIG. 1.
Figure 2A:
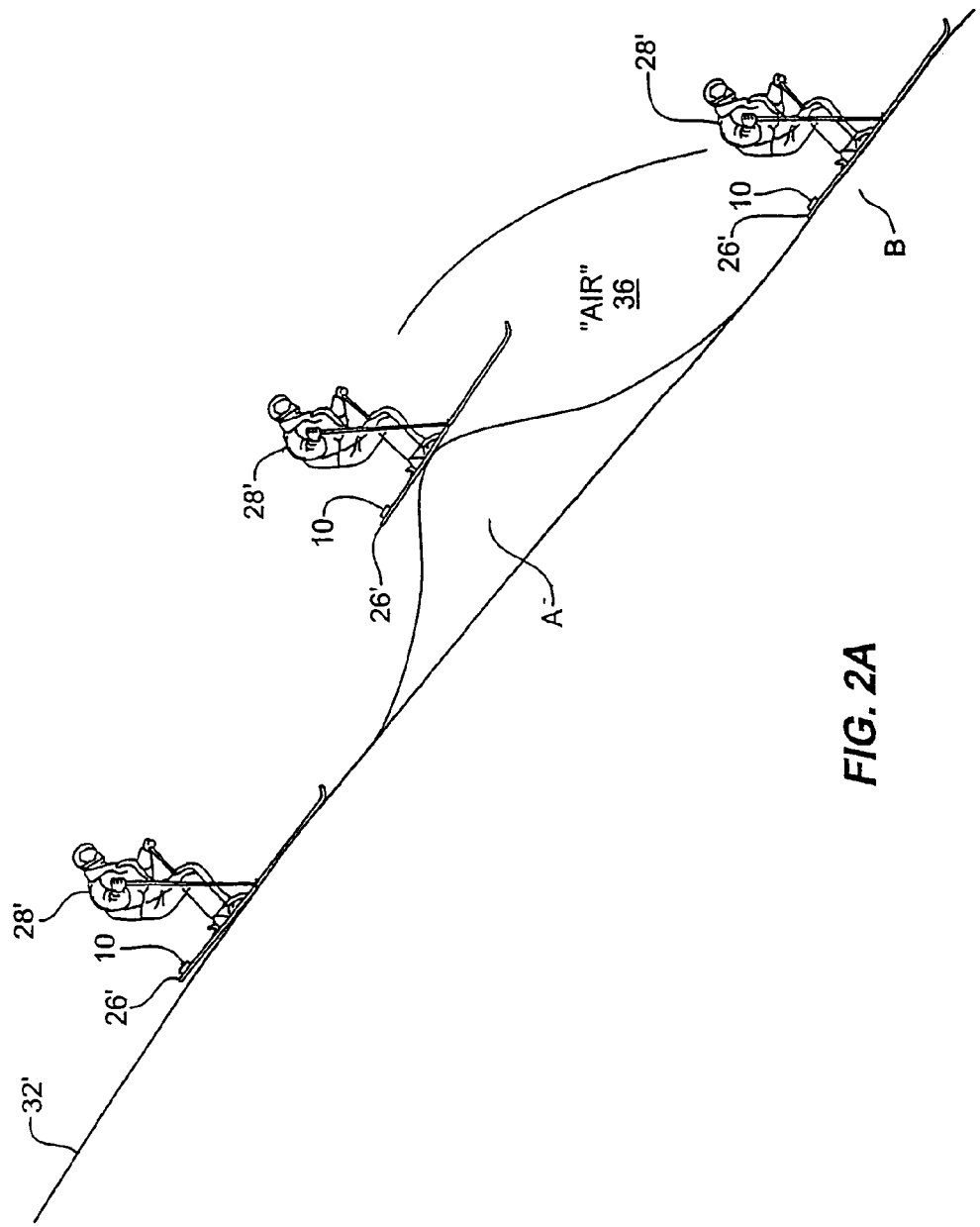
Figure 2B:
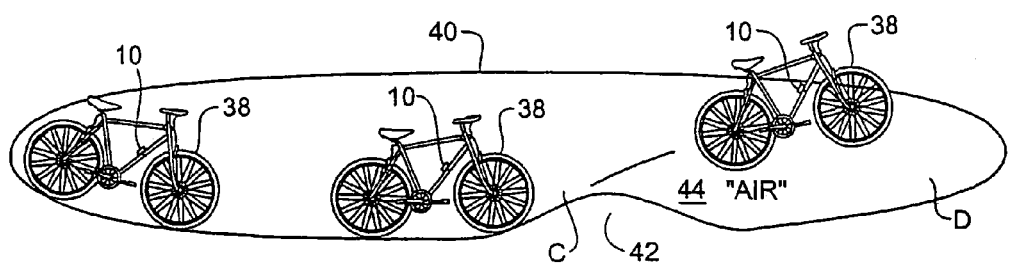

FIGS. 2, 2A and 2B show typical uses of the system 10 illustrated in FIG. 1. In particular, FIG. 2 shows the system 10 mounted onto a ski 26. As is normal, the ski 26 is mounted to a skier 28 (for illustrative purposes, the skier 28 is only partially illustrated), via a ski boot 30 and binding 30a, and generally descends down a ski slope 32 with a velocity 34. Accordingly, one use of the system 10 is to calculate the peak speed of the ski 26 (and hence the skier 28) over a selectable period of time, e.g., during the time of descent down the slope 32.

Another use of the system 10 of FIG. 1 is to calculate the loft, or "air" time of the ski 26 (and hence the user 28) during the descent down the slope 32. Consider, for example, FIG.

2A, which illustrates the positions of the ski 26' and skier 28' during a lofting maneuver on the slope 32'. The ski 26' and skier 28' speed down the slope 32' and launch into the air 36 at position "a," and later land at position "b" in accord with the well-known Newtonian laws of physics. The system 10 calculates and stores the total "air" time that the ski 26' (and hence the skier 28') experience between the positions "a" and "b" so that the skier 28' can access and assess the "air" time information.

FIG. 2B illustrates the system 10 mounted onto a mountain bike 38. FIG. 2B also shows the mountain bike 38 in various positions during movement along a mountain bike race course 40 (for illustrative purposes, the bike 38 is shown without a rider). At one location "c" on the race course 40, the bike 38 hits a dirt mound 42 and catapults into the air 44. The bike 38 thereafter lands at location "d." As above, the system 10 provides information to a rider of the bike 38 about the speed attained during the ride around the race course 40; as well as information about the "air" time between location "c" and "d."

USER INTERFACE AND DISPLAY

With further reference to FIG. 1, the display 16 can be one of any assortment of displays known to those skilled in the art. For example, liquid crystal displays (LCDs) are preferred because of their low power draw (for example, LCDs utilized in digital watches and portable computers are appropriate for use with the invention). Other suitable displays can include an array of light emitting diodes (LEDs) arranged to display numbers.

Figure 3:
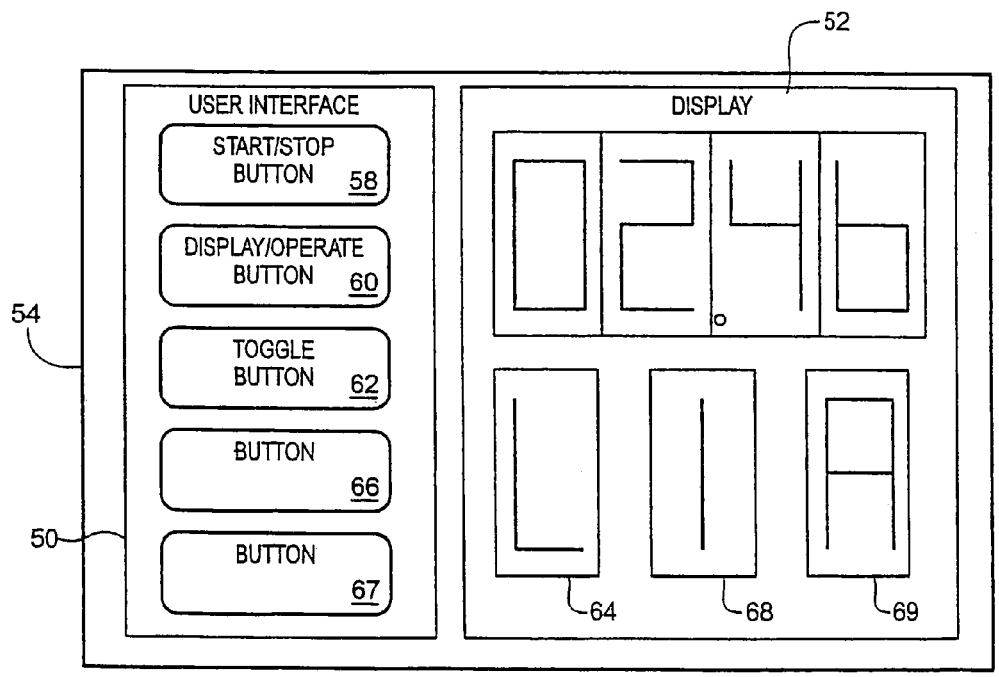
FIG. 3 illustrates a user interface and display suitable for use in the system of FIG. 1.

FIG. 3 illustrates a user interface 50 and display 52 constructed according to the invention and which are suitable for use, respectively, as the interface 14 and display 16 of FIG. 1. Outline 54 illustrates the outline of a system constructed according to the invention, e.g., the housing outline 24 of the system 10 of FIG. 1. In order for a user of the system to access information within the system, user interface 50 includes control buttons. For example, with reference to FIG. 3, one embodiment of the user interface 50 includes a start/stop button 58, a display-operate button 60, and a speed/loft toggle button 62. These buttons operate as follows:

- A user presses the start/stop button 58 at the start of activity—such as at the start of skiing down a slope or biking down a trail—and presses the button 58 at the completion of activity to cease the acquisition of data (as described in more detail below).
- A user pressed the display-operate button 60 to activate the display 52 so that a user can view recorded information from the sporting activity on the display 52. Accordingly, the display 52 is normally OFF—and not drawing power from the associated power source (e.g., the power source 22 of FIG. 1)—and is turned ON only when a user activates the display-operate button 52. The ON and OFF display conditions are preferably obtained in one of two ways: in one embodiment of the invention, the display 52 automatically turns OFF after a preselected time through the control of the microprocessor subsystem 12 of FIG. 1; or, in an alternative embodiment, the display 52 remains activated until a user again presses the display-operate button 60.
- A user presses the speed/loft toggle button 62 to sequentially command the display, respectively, of information about speed and loft time. For example, if the display 52 currently displays speed information, a user can instead command the display of loft time information by pressing the speed/loft toggle button 62 once. If, on the other hand, the display 52 currently displays loft information, a user can instead command the display of speed information by pressing the speed/loft toggle button 62 once. Preferably, one portion 64 of the display denotes whether speed or loft information is being displayed. For example, as illustrated, a "L" letter denotes that loft information is being displayed. An "S" letter likewise denotes that speed information is being displayed. For illustrative purposes, the "air" time is also displayed in FIG. 3 as 2.46 seconds, which represents the "air" time of a typical ski jump.

It is important to note that one embodiment of the invention does not include the speed/loft toggle button 62 because, as noted earlier, certain embodiments of the invention do not include both the speed sensor and loft sensor. In such an embodiment, it is unnecessary to include a toggle button 62.

The display 52 of FIG. 3 also shows another feature of the invention, namely that a system constructed according to the invention preferably calculates and stores successive records relating to speed and loft information relative to a user's activity. For example, a skier may catch "air" time more than once during a given activity; and the system of the invention can store successive loft times for access by the user. Most often, the peak "air" time is displayed, by default. However, certain users wish to evaluate successive loft time information and, accordingly, the system 10 of FIG. 1 preferably determines and stores the successive information (described in greater detail below). A user can access the successive loft time information by toggling a combination of the buttons 58-62, such as known to those skilled in the art (e.g., a combination of holding one button down while pressing another button); or by including yet another button 66 on the user interface 50. A display portion 68 of the display 52 shows a number corresponding to the sequential information on display. For example, the illustrated "1" number means that the highest "air" time record is currently being displayed; while a number greater than one means that a loft time other than the highest loft time is being displayed. In addition, the highest number displayed within the portion 68 refers to the total number of "air" times for the selected activity period (thus for example a user can determine the total number of jumps achieved for a given day).

In still another embodiment of the invention, successive speed information can be displayed much the way successive "air" time information is stored and displayed, described above. To view the speed information, the speed/loft toggle button 62 is pressed once to display "S" in the display portion 64, and a user can toggle button 66 to view the successive speed records as denoted by the number in display portion 68. However, this information is not deemed very useful except under a very few circumstances—since a user generally moves with some velocity during a given activity—and thus, generally, the peak speed achieved during a given activity is normally displayed on the display 52 when commanded by the speed/loft toggle button 62.

In an alternative embodiment, a button 67 is used to alter the modes of the system so that other information such as average "air" time may be calculated and displayed by the invention. For example, FIG. 3 illustrates a display portion 69 that shows a letter "A," corresponding to information relating to averages. Thus, for a particular sporting activity, a user can press button 69 to display "air" time as a running average of all the successive "air" times (in such an embodiment, the display portion 68 is preferably OFF because the information displayed in portion 68 refers to successive peak information). To access the peak "air" time information, the button 67 is pressed once again, causing the microprocessor subsystem 12 to change the display information from integrated average values to peak values (accordingly, the display portion 69 preferably shows a "P" to identify to the user that peak information is being displayed; and the display portion 68 is preferably ON in this "peak" mode to denote which successive record is being displayed). To access integrated information—e.g., the total "air" time for a given day—the button 67 is pressed once again, causing the microprocessor subsystem 12 to show the integrated "air" or speed information (depending on the toggle of the speed/loft toggle button 62). Integrated values are preferably displayed by indicating to the user a "T" (for total) in the display portion 69.

It should be clear to those skilled in the art that other buttons and/or combinations of buttons can be incorporated within the user interface 50 within the scope of the invention. The microprocessor subsystem 12 of FIG. 1 stores much information during the sporting activity and which can be converted to different forms, e.g., averages, peaks, and totals. In accord with the invention, different buttons and combinations of buttons can be used to access all of the available information. In addition, other information can be denoted, for example, within the display portion 69 to identify the different types of information available within the system.

For example, yet another form of information which may be of interest to sporting persons is the "dead" time, i.e., the time that the person is not skiing or biking during the day. For example, a person who hangs out in the bar during part of the afternoon will not have a high efficiency factor for actual ski time as compared to the available ski time. This efficiency information is available in accord with the invention because the microprocessor subsystem 12 of FIG. 1 preferably includes a clock element (readily known to those skilled in the art) for indicating processed time over a selectable period (the microprocessor subsystem 12 can in fact include a 24-hour clock element, much the way a digital wrist-watch includes 24-hour information). Accordingly, a user can start the system 10 of FIG. 1 at the beginning of the day by pressing the start/stop button 58, and stop the collection of data at the end of the day by again pressing the start/stop button 58. The microprocessor subsystem 12 keeps track of the elapsed time between the start and stop of the system (i.e., the selectable time period), thereby providing means for determining the user's "dead" time for the day. That is, the microprocessor subsystem 12 calculates "dead" time by intelligently calculating the total time lapse within which a vibrational noise spectrum (described in more detail below in connection with FIG. 4) is present within the selectable time period; and dividing that total time lapse by the selectable time period to obtain a ratio of the real activity time versus the user's dead time (for example, a ratio of 80% means that the sporting person skied for 80% of the day). Dead time information is thereafter easily determined by subtracting 80% from 100%, to get 20% dead time. The dead time information is shown, for example, by toggling the button 67 to a dead time mode, denoted as "D," in the display portion 69, and displaying the dead time as a percentage in the display 52. Alternatively, the real activity time is displayed as a percentage in the display 52 by toggling the button 69 until "R" shows up in the display portion 69.

LOFT SENSOR

With further reference to FIG. 1, the loft sensor 20 may be constructed by several known components. Preferably, the sensor 20 is either an accelerometer or a microphone assembly. Alternatively, the sensor 20 may be constructed as a mechanical switch that detects the presence and absence of weight onto the switch. Each of these alternatives is described below.

Loft Sensor: Accelerometer Embodiment

An accelerometer, well known to those skilled in the art, detects acceleration and provides a voltage output that is proportional to the detected acceleration. Accordingly, the accelerometer senses vibration—particularly the vibration of a vehicle such as a ski or mountain bike—moving along a surface, e.g., a ski slope or mountain bike trail. This voltage output provides an acceleration spectrum over time; and information about loft time can be ascertained by performing calculations on that spectrum. Specifically, the microprocessor subsystem 12 of FIG. 1 stores the spectrum into memory 13 and processes the spectrum information to determine "air" time.

Figure 4:
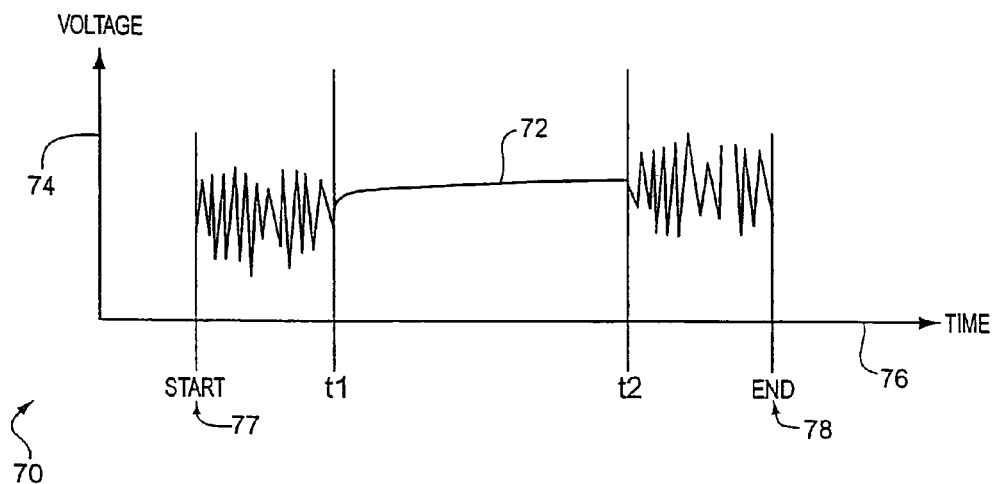
FIG. 4 is a representative vibrational spectrum, shown illustratively, for calculating "air" or loft time in accord with the invention.

FIG. 4 illustrates a graph 70 of a representative vibrational spectrum 72 that is stored into the microprocessor subsystem 12 (FIG. 1). The vertical axis 74 of the graph 70 represents voltage; while the horizontal axis 76 represents time. At the beginning of activity 77—such as when a user of a system constructed according to the invention presses the start/stop button 58 (see FIG. 3)—the loft sensor 20 of FIG. 1 begins acquiring data and transferring that data to the microprocessor subsystem 12 via communication lines 11b. This data appears highly erratic and random, corresponding to the randomness of the surface underneath the vehicle (e.g., ski or vehicle). At time "t1," the user of the system lofts into the air, such as illustrated as location "a" in FIG. 2A and as location "c" in FIG. 2B; and lands some time later at time "t2," such as illustrated as location "b" in FIG. 2A and as location "d" in FIG. 2B. The vibrational spectrum between t1 and t2 is comparatively smooth as compared to the spectrum outside this region because the user's sporting vehicle (e.g., the ski or mountain bike) is in the air and is not therefore subjected to the random vibrations of the road or ski slope. Accordingly, this relatively smooth spectrum between t1 and t2 can be readily discerned from the rest of the spectrum by the microprocessor subsystem 12 and evaluated for "air" time: specifically, "air" time is t2-t1.

FIG. 4 also shows that the spectrum stops at the end 78 of the sporting activity, such as when the user of the system again presses the start/stop button 58, FIG. 3.

In one embodiment of the invention, a user can simply start the system 10 of FIG. 1 at the beginning of the day, by toggling the start/stop button 58, and stop the system 10 at the end of the day, by again toggling the start/stop button 58. The issue here, however, is that there may be apparent "air" times between the starting and stopping of the system which is not, in fact, the "air" time of interest. For example, standing in line at a ski lift represents a period within which the spectrum 72 appears smooth, and might be mistaken for "air" time. Accordingly, the microprocessor subsystem 12 of the invention preferably includes process boundary conditions within which "air" time will be excluded. For example, one practical boundary condition is: if the spectrum between any given "t1" and "t2" time (FIG. 4) is greater than five seconds, then exclude that time from memory as actual "air" time. Thus, each time the skier stands in line, that smooth spectrum which is being processed by the system is ignored.

Another boundary condition, for example, concerns the type of skier using the system. Some skiers often make quick jump turns down the mountain. These would normally show up as mini "air" times. Thus, in accord with another aspect of the invention, another boundary condition is: if the spectrum between any given "t1" time and "t2" time (FIG. 4) is less than 500 ms, then exclude that time from memory as actual "air" time. Accordingly, each jump turn will not be included in the total "air" time for the day, as is expected by users of the system.

The invention preferably includes an adjustment mechanism to adjust these boundary conditions (e.g., the five seconds maximum and the 0.5 second minimum) so that such conditions can be adjusted and optimized to individual users. Accordingly, in one embodiment of the invention, certain of the buttons 58-67 of FIG. 3 can be used in combination to set the maximum and minimum boundary conditions. Alternatively, one or more additional buttons can be included within the user interface of FIG. 3 to provide the adjustment mechanism.

Another embodiment of the invention internally resets the start/stop button 58 when the system senses the lack of spectral information for a preselected period of time. Thus, after the preselected period, the system has an automatic time-out, resulting in the microprocessor subsystem 12 resetting itself as if the start/stop button 58 were pushed.

Accelerometers are commercially available and are relatively cheap items. They are also small, so that all of the components 12, 14, 16 and 20 may easily fit within a small, lightweight housing. Suitable accelerometers include those accelerometers shown and described in connection with FIGS. 13, 14 and 14A.

Loft Sensor: Microphone Embodiment

A microphone, also well known to those skilled in the art, detects sound waves and provides a voltage output that is responsive to the detected sound waves. Accordingly, a microphone, like the accelerometer, senses the vibration of a vehicle, such as a ski or mountain bike, moving along a surface, e.g., a ski slope or mountain bike trail. By way of analogy, consider putting one's ear flat onto a desk and running an object across the desk. As one can readily determine, the movement of the object on the desk is readily heard in the ear. Likewise, a microphone as the loft sensor 20 readily "hears" the vibrational movements of the vehicle on the surface. Therefore, like the aforementioned accelerometer, a vibrational spectrum such as shown in FIG. 4 is generated by the microphone loft sensor during a user's sporting activity. As above, the microprocessor subsystem 12 utilizes the spectrum to determine "air" time.

Like accelerometers, microphones are also commercially available and are relatively cheap. They are also small, so that all of the components 12, 14, 16 and 20 may easily fit within a small, lightweight housing.

Figure 5:
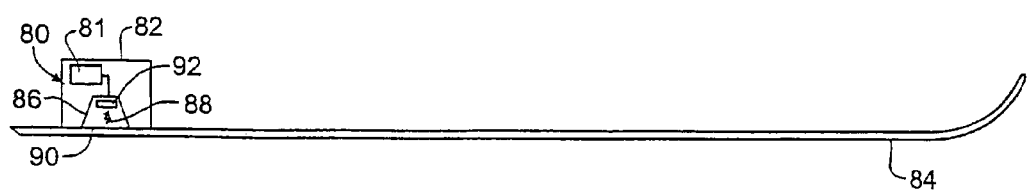
FIG. 5 shows a microphone-based loft sensor constructed according to the invention and which is suitable for use in the system of FIG. 1.

FIG. 5 illustrates one embodiment of a microphone assembly 80 suitable for use with the invention. Specifically, a system 82 constructed according to the invention mounts, for example, to a ski 84 (for illustrative purposes, only the loft sensor portion 80 and microprocessor subsystem 81 are shown as part of the system 82 even though other components such as the display and user interface are present within the system 82). The microphone assembly 80 preferably includes a tube portion 86 to funnel the sound waves 88 coming from the ski surface 90 to the microphone element 92, e.g., a piezoelectric element known to those skilled in the art. During operation, the vibrational motion caused by the ski's interaction with the surface underneath the ski generates the sound waves 88 detected by the element 92, which converts the sound waves to voltages. These voltages are sampled and stored in the microprocessor subsystem 12 so that the information can be processed to extract the "air" information.

Depending on the sensitivity of the accelerometers and microphone assemblies, described above, it is feasible to attach the system of the invention directly to a user of the system as opposed to the vehicle. The vibrational or sound information is transmitted through the user to some degree while the user is on the ground, and such information can be used, as above, to calculate "air" time. Accordingly, one embodiment of the invention includes a system which measures "air" time that mounts directly to a user rather than to the vehicle, e.g., a ski.

Loft Sensor: Weight Switch Embodiment

In still another embodiment of the invention, the sensor 80 of FIG. 1 can be a switch that rests below the boot of the ski, e.g., the boot 30 of FIG. 2, and that senses pressure caused by the weight of the user within the boot. That is, when the skier is on the ground, the boot squeezes the switch, thereby closing the switch. The closed switch is detected by the microprocessor subsystem 12 (FIG. 1) as a discrete input. When a skier jumps into the air, the switch opens up by virtue of the fact that relatively no weight is on the switch; and this opened switch is also detected and input into microprocessor subsystem 12. The microprocessor subsystem 12 will count at known time intervals (clock rates) for the duration of the opened switch, corresponding to the jump, and will record how long the jump lasts.

As described in connection with FIG. 3, the "air" time may be recorded as a single jump, or recorded as a successive list of jumps. In addition, the "air" time can be summed or integrated into a running total, such as described above.

Figure 6:
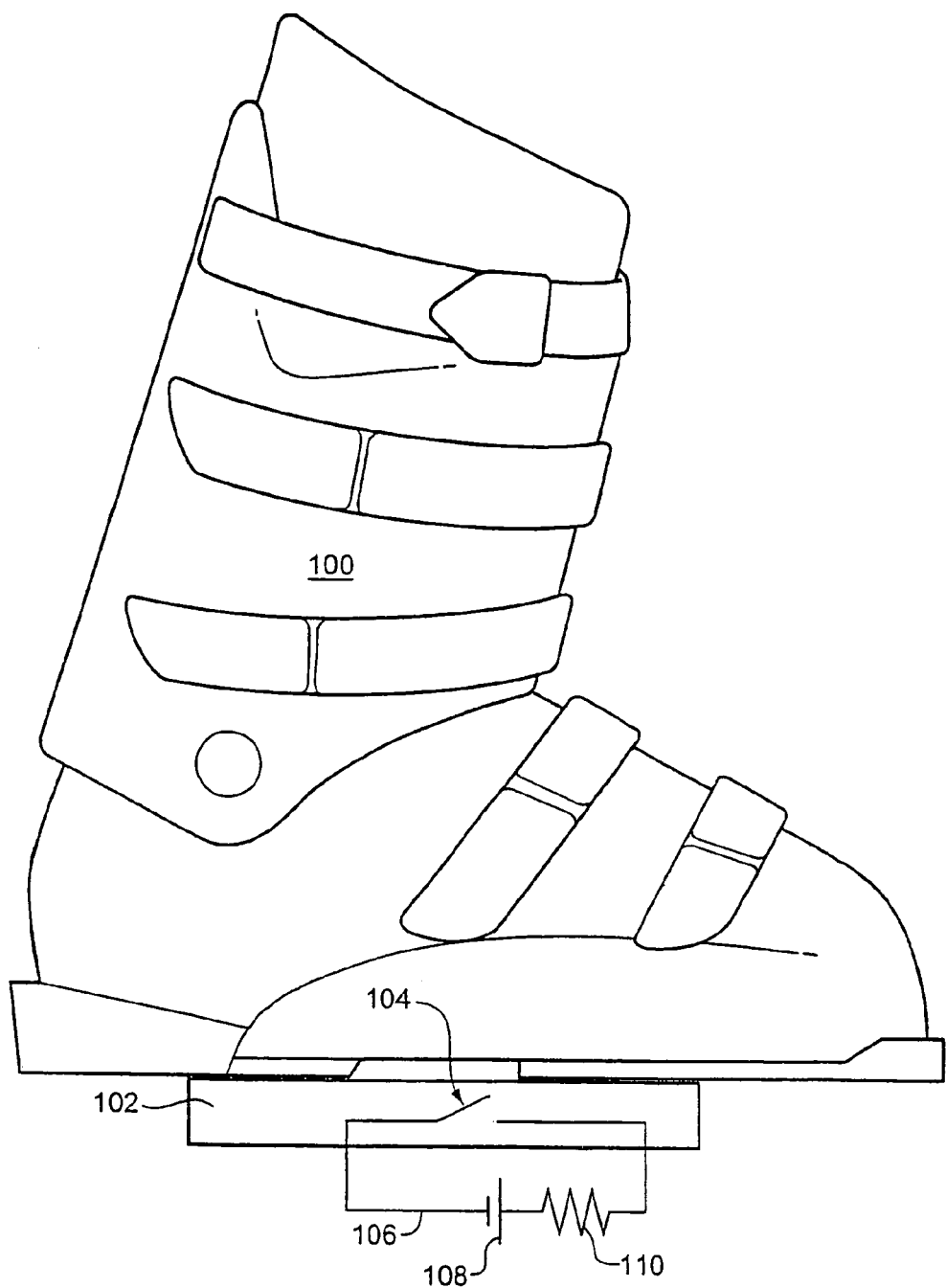
FIG. 6 shows a switch-based loft sensor constructed according to the invention and which is suitable for use in the system of FIG. 1.

FIG. 6 illustrates the manner in which one switch is formed, in accord with the invention (for illustrative purposes, the drawing of FIG. 6, like most of the drawings herein, are not to scale; and further shows disproportionate sizes of elements of the invention at least). A boot 100 (e.g., the ski boot 30 of FIG. 2) rests on top of a compressible material 102, e.g., foam, that includes a switch 104. When the user steps on the compressible material 102, the compressible material 102 compresses and causes the switch 104 to close, completing the circuit 106 (for illustrative purposes, the circuit 106 is shown simply as a switch 104, battery 108 and resistor 110; and the circuit 106 is shown externally when in fact the circuit is within the system of the invention and in communication with the microprocessor subsystem 12). When the switch 104 is closed, the circuit is in an ON condition, and when the switch 104 is not closed, the system is in an OFF condition. Accordingly, the microprocessor subsystem 12 senses the ON and OFF conditions to calculate "air" time. Specifically, the time between an OFF condition and an ON condition can be used to determine "air" time.

Figure 7:
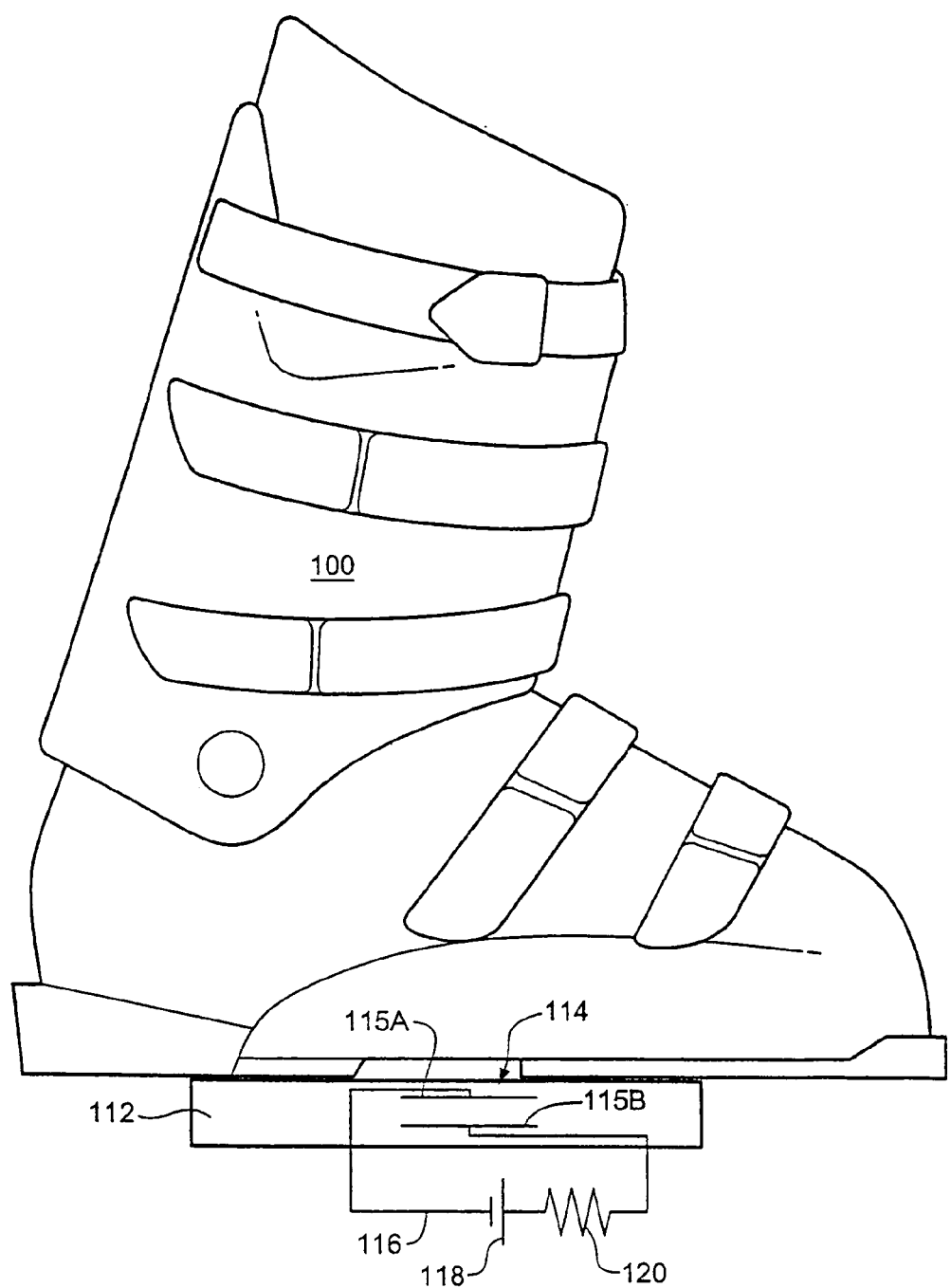
FIG. 7 shows a capacitance-based loft sensor constructed according to the invention and which is suitable for use in the system of FIG. 1.
Figure 8:
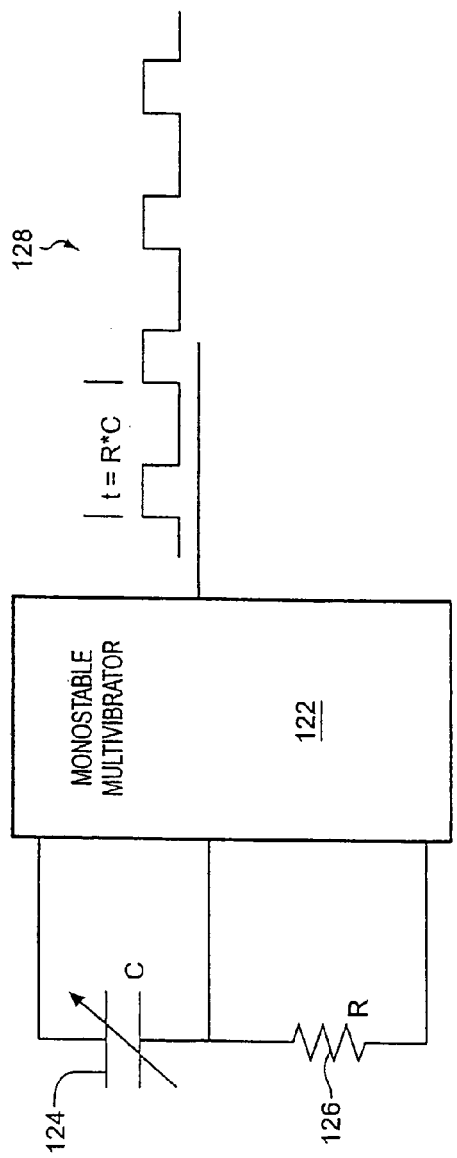
FIG. 8 schematically illustrates electronics, constructed according to the invention, for converting a varying capacitance, e.g., the capacitance derived from the loft sensor of FIG. 7, to information suitable for calculating "air" time.

Another embodiment of the invention which is suitable for use as the loft sensor 20, FIG. 1, includes a pad that is placed under the skier's boot and that changes capacitance as a function of a change of applied pressure. For example, consider FIG. 7 (again with illustrative ski boot 100) which shows a compressible material 112 and a capacitance-changing element 114 that changes capacitance under varying applied pressures. This capacitance-changing element 112 is connected in circuit 116, including the illustrative battery element 118 and resistor 120, with the system of the invention such that its capacitance is converted to a digital signal by conditioning electronics, such as shown in FIG. 8. As above, the circuit of FIG. 7 is shown illustratively and without the other necessary components (e.g., the microprocessor subsystem) of the invention. Those skilled in the art understand that the components 112, 114, 115, 116, 118 and 120 connect integrally with a system (e.g., the system 10 of FIG. 1) constructed according to the invention.

By way of background, a capacitor consists of two parallel plates separated by a dielectric material. The capacitance is directly proportional to the cross sectional area of the plates and inversely proportional to the distance between the plates. When the dielectric is the compressible material 112, FIG. 7, then the pressure applied to the material 112 changes the distance between the plates 115a, 115b of the capacitance-changing element 114, thereby proportionately increasing the capacitance.

FIG. 8 shows a monostable multivibrator 122, e.g., a NE555, in accord with the invention which converts the varying capacitance (illustrated as portion 124) from the capacitance-changing element 114 of FIG. 7 to information suitable for calculating "air" time. A resistor 126 connects in circuit with the portion 124 and the multivibrator 122. The output pulse train 128 is directly dependent on the product of the resistance "R" and variable capacitance "C". The resistance R may be fixed while the capacitance C is dependent on the pressure exerted on the pad 112 thus shifting the frequency of a pulse train 128. The pulse train 128 repetition rate is indicative of the value of capacitance of 124. When the pulse train 128 repetition rate increases the value of C 124 has decreased and the skier's boot is applying less pressure on the pad 112. This event marks the beginning of the "air time" measurement. When the pulse train 128 repetition rate decreases, meaning a sudden increase of capacitance, the boot is now applying greater pressure on the ski, signifying the end of the "air" time measurement. The length of time that the pulse train 128 remains at the higher repetition rate is equal to the amount of time the ski is off the ground. That amount of time is the loft or "air" time.

Figure 9:
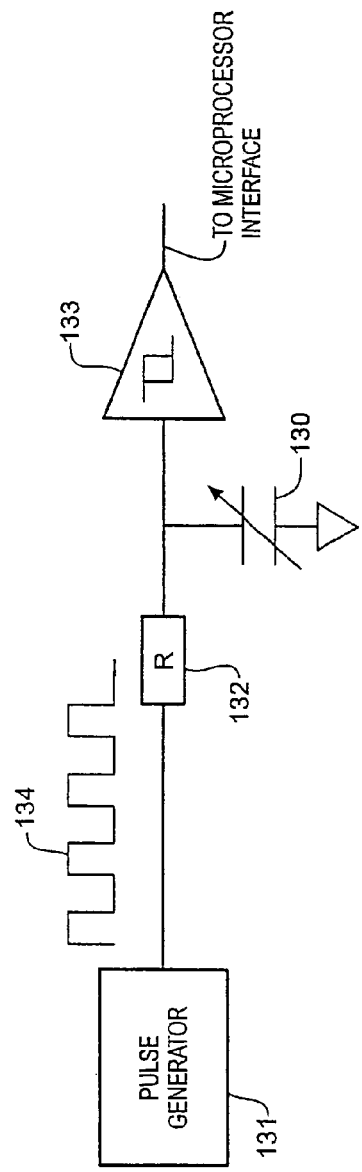
FIG. 9 schematically illustrates alternative electronics, constructed according to the invention, for converting a varying capacitance, e.g., the capacitance derived from the loft sensor of FIG. 7, to information suitable for calculating "air" time.

Alternatively, and such as shown in FIG. 9, the change in capacitance can be used in a filter which passes a pulse train during low capacitance levels (no boot pressure) and which filters out the pulse train during high capacitance events (high boot pressure). For example, a capacitance-changing element 130 (e.g., the capacitance-changing circuit 116 of FIG. 7) connects to the input of a Schmidtt Trigger CMOS gate 133 and ground. A pulse generator 131 connects through a fixed resistor R 132 to the capacitance-changing element 133 and the Schmidtt Trigger CMOS gate 133. The pulse generator 131 produces a steady pulse train 134. When the capacitance changing element 130 is at a high capacitance, corresponding to a high boot pressure meaning that the ski is on the ground, the combination of the fixed resistance R 132 and the capacitance of the capacitance-changing element 130 absorbs the pulse train and the output of the Schmidtt Trigger CMOS gate 133 is constant. On the other hand, when the skier takes flight, the capacitance of the capacitance-changing element 130 is low, thus allowing the pulse train 134 to pass through to the Schmidtt Trigger CMOS gate 133 input. The output of the Schmidtt Trigger CMOS gate 133 in this latter case toggles at the same rate as the pulse train 131, thereby identifying a condition of "air" time. A discrete input is thus used by the processor to sample for the existence of the pulse train to calculate "air" time.

MICROPROCESSOR SUBSYSTEM

The microprocessor subsystem 10 of FIG. 1 can include a microcontroller element, a microcontroller element with reduced functionality to conserve power, or a microprocessor element with associated memory and logic to perform the requisite calculations of the invention, including the processing power to drive the display 16 and user interface 14.

Figure 10:
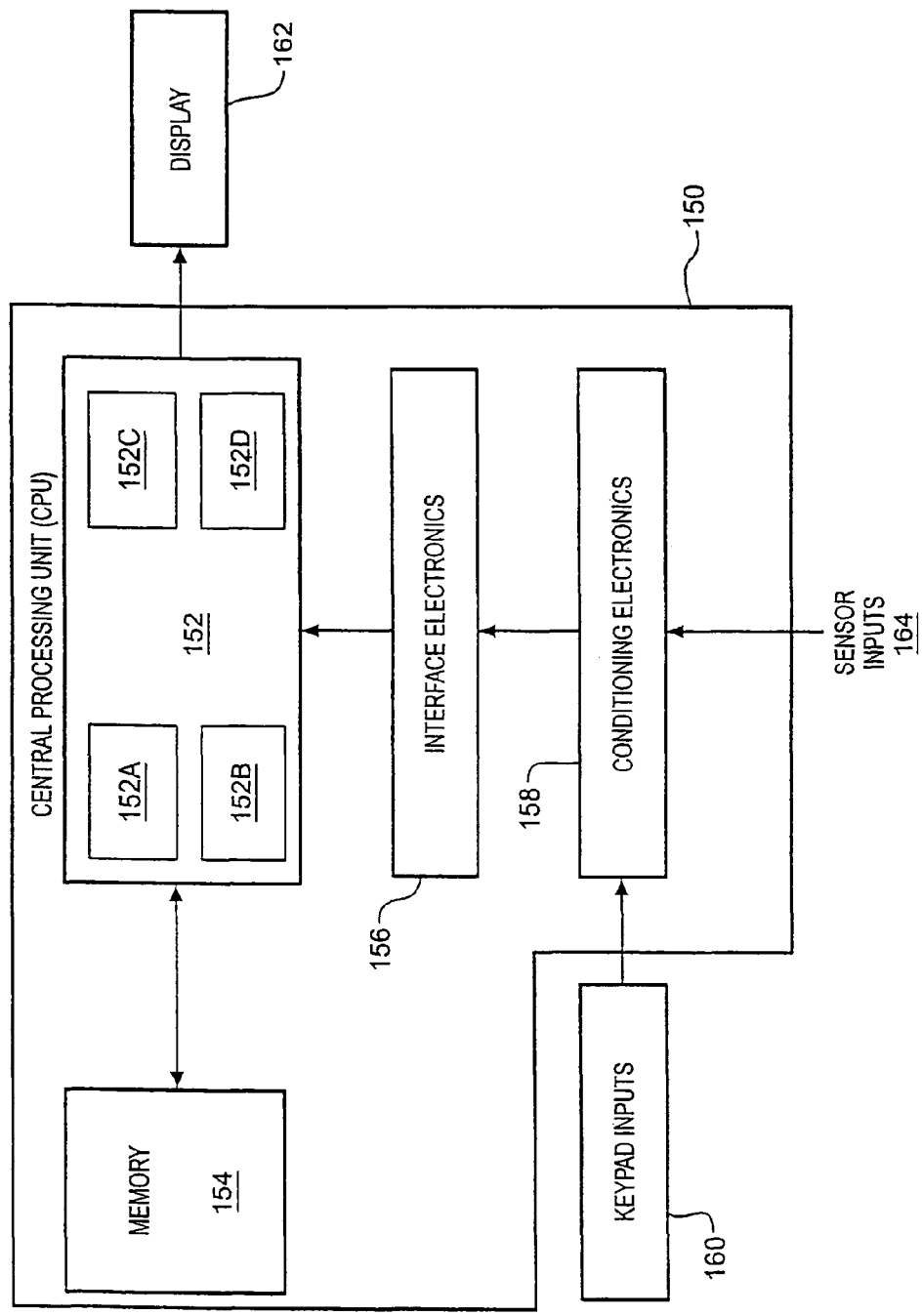
FIG. 10 schematically illustrates a microprocessor subsystem constructed according to the invention and which is suitable for use in the system of FIG. 1.

Preferably, however, the microprocessor subsystem 12 is constructed by several known components, such as shown in FIG. 10. FIG. 10 shows microprocessor subsystem 150 constructed according to the invention and including a Central Processing Unit (CPU) 152, memory 154, interface electronics 156, and conditioning electronics 158. The user interface 160, such as the interface 14 of FIG. 1, and including the button inputs of FIG. 3, connects to the subsystem such as shown and directly to the conditioning electronics 158. The display 162, such as the display 16 of FIG. 1, preferably connects to the subsystem such as shown and directly to the CPU 152.

The CPU 152 includes a microprocessor 152a, Read Only Memory (ROM) 152b (used to store instructions that the processor may fetch in executing its program), Random Access Memory (RAM) 152c (used by the processor to store temporary information such as return addresses for subroutines and variables and constant values defined in a processor program), and a master clock 152d. The microprocessor 152a is controlled by the master clock 152d that provides a master timing signal used to sequence the microprocessor 152a through its internal states in its execution of each processed instruction. The clock 152d is the master time source through which time may be deduced in measuring velocity or air time (for example, to determine the elapsed time from one event to another, such as the lapsed time "t1" to "t2" of FIG. 4, the clock rate provides a direct measure of time lapse).

The microprocessor subsystem 150, and especially the CPU 152, are preferably low power devices, such as CMOS; as is the necessary logic used to implement the processor design.

The subsystem 150 stores information about the user's activity in memory. This memory may be external to the CPU 152, such as shown as memory 154, but preferably resides in the RAM 152c. The memory may be nonvolatile such as battery backed RAM or Electrically Erasable Programmable Read Only Memory (EEPROM). External signals 164 from the speed and/or loft sensors, e.g., the speed sensor 18 and loft sensor 20 of FIG. 1, are connected to the conditioning electronics 158 which filters, scales, and, in some cases, senses the presence of certain conditions, such as zero crossings. This conditioning essentially cleans the signal up for processing by the CPU 152 and in some cases preprocesses the information. These signals are then passed to the interface electronics 156, which converts the analog voltage or currents to binary ones and zeroes understood by the CPU 152.

The invention also provides for intelligence in the signal processing, such as achieved by the CPU 152 in evaluating historical data. For example, "air" time may be determined by the noise spectra that changes abruptly, such as indicating a leap, instead of a noise spectra representing a more gradual change that would occur for example when a skier slows to a stop. As previously noted, a minimum quiet time is required, in certain embodiments of the invention, to differentiate between "air" time and the natural motions associated with turning and skiing (e.g., jump skiing). Further, in other certain embodiments, a maximum time is also programmed to differentiate "air" time from an abrupt stop, such as standing in a lift line.

SPEED SENSOR

In accord with the invention, if speed is calculated within the system, the speed sensor 118 of FIG. 1 can take one of several forms, including: (1) a pitch detection system that detects the "pitch" of the vibrational spectrum and that converts the pitch to an equivalent speed; (2) a laser-based or sound-based Doppler-shift sensor; (3) an accelerometer-based speed sensor; (4) a pressure-based speed sensor; and (5) a voltage-resistance sensor.

It should be noted that in either of the speed or loft sensors, it may be preferable to incorporate state machine logic within the sensor in order to preprocess the data for the microprocessor subsystem. Thus, in accord with the invention, processing logic such as described herein in connection with the microprocessor subsystem can be incorporated, at least in part, within one or both of the speed and loft sensors. Because of the complexity of the speed sensor, such preprocessing power is more appropriately within the speed sensor.

Speed Sensor: Pitch Detection

In accord with this embodiment, no separate speed sensor element, e.g., the sensor 18 of FIG. 1, is required. Rather, the vibrational spectrum that is generated by the loft sensor 20, and particularly the accelerometer or microphone embodiment discussed in connection with FIG. 4, will be used to determine the pitch of the vibration and, thereby, the equivalent speed. By way of example, note that a skier generates a scraping sound on hard-packed snow and ice. When the skier changes velocity, that scraping sound changes in pitch. The spectrum shown in FIG. 4 outside the t1/t2 region (but within the "start" and "end" region) is, effectively, that pitch. By calibrating the microprocessor subsystem 12 to associate one pitch as one velocity, and so on, the speed of the vehicle (e.g., ski and mountain bike) may be determined by spectral content.

In accord with the invention, one method for determining the "pitch" of the spectrum outside the t1/t2 loft region of FIG. 4 (and within the start/stop time) is to determine the "best fit" sine wave to the vibrational spectrum data. This sine wave will have a frequency, or "pitch" that may be quantified and used to correlate velocity.

This spectral content may be determined, in part, by the conditioning electronics 158 of FIG. 10 such to determining rise times to infer a bandwidth of the information. The conditioning electronics 158 and/or CPU 152 can also measure the time between successive zero crossings, which also determines spectral content.

Figure 11:
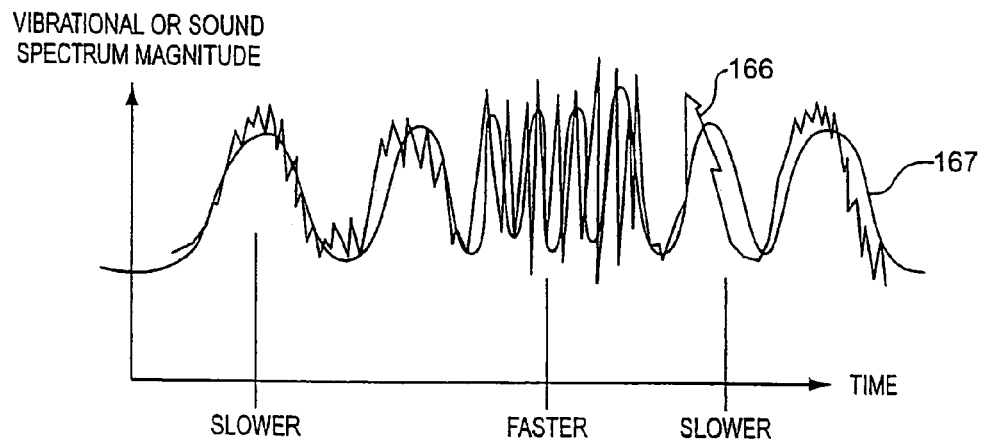
FIG. 11 illustrates one exemplary pitch-detection process, in accordance with the invention, which is used to determine the speed of a vehicle.
Figure 13:
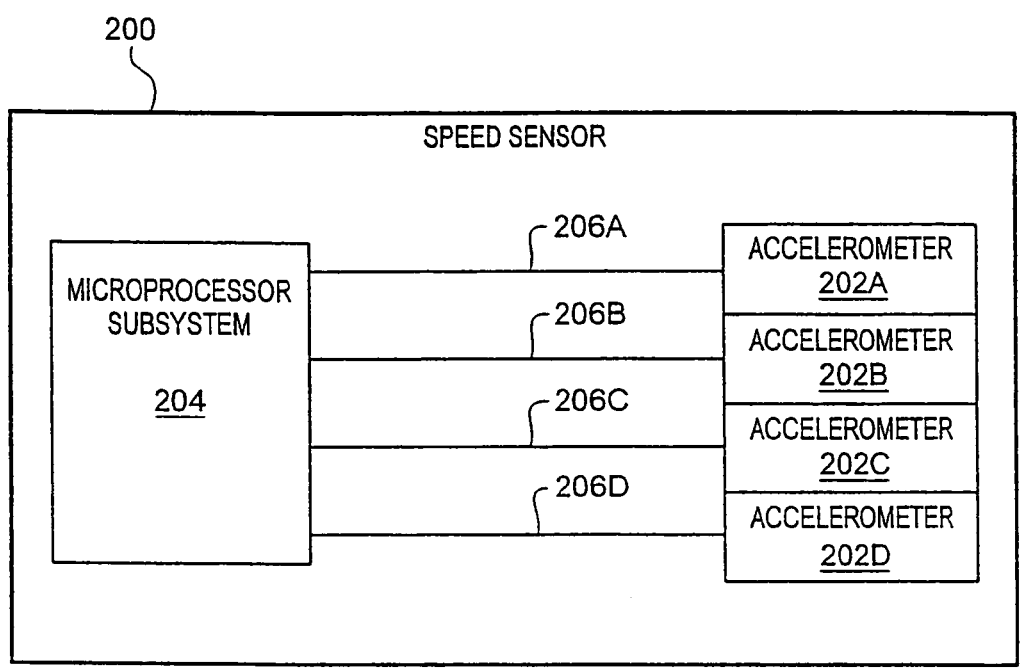
FIG. 13 illustrates an accelerometer-based speed sensor constructed according to the invention and which is suitable for use as both the speed and loft sensors of FIG. 1.

For example, FIG. 11 illustrates a spectrum 166 generated from a sensor such as a sensor 18 or 20 (FIG. 1), or 82 (FIG. 5), or 202a-202d (FIG. 13 below). The spectrum 166 thus represents an acceleration spectrum or sound spectrum such as described herein. The microprocessor subsystem 12 of FIG. 1 evaluates the spectrum 166 and generates a best-fit sine wave 167 to match the primary frequency of the spectrum 166 over time. FIG. 11 shows illustratively a situation where a vehicle, such as a ski, moves slowly at first, corresponding to a lower sine-wave frequency, then faster, corresponding to a higher frequency sine wave, and then slower again. This pitch transition is interpreted by the microprocessor subsystem (e.g., the subsystem 12 of FIG. 1) as a change of speed. Specifically, the microprocessor subsystem of the invention is calibrated in this embodiment to associate a certain frequency with a certain speed; and speed is thus known for the variety of pitches observed during an activity, such as illustrated in FIG. 11.

It should be noted that the pitch information is surface dependent (and vehicle dependent). That is, a ski-over-snow-speed-spectrum has a different spectrum than a bicycle-over-ground-spectrum. Accordingly, different calibrations must be made for different vehicles and speeds, in accord with the invention. Further, certain spectrums may actually decrease in frequency as speed increases; which also must be calibrated to obtain the correct speed information. These calibrations are typically programmed into the microprocessor subsystem memory, e.g., the memory 13 of subsystem 12 of FIG. 1. Further, in certain embodiments of the invention, the system stores different spectrum calibrations for different activities so that a user can move the system from one sport to another. Accordingly, one or more buttons such as the buttons 58-67 of FIG. 3 are introduced to the user interface, such as known to those skilled in the art, in order to selectively access the different spectrum calibrations.

Speed Sensor: Doppler-based

It is well known that Doppler radar is used by police vehicles to detect speed. In accord with this embodiment of the invention, the same principles apply to the measurement of speed of the sporting vehicle. For example, consider FIG. 12.

Figure 12:
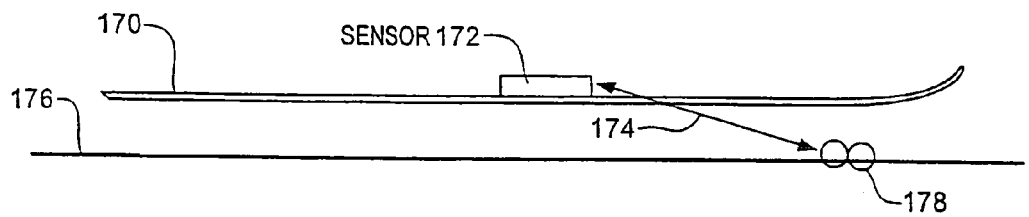
FIG. 12 illustrates a Doppler-based approach to sensing speed in accordance with the invention.

FIG. 12 shows a representative ski 170 (partially shown) with a Doppler-based sensor 172 mounted thereon (for illustrative purposes, the Doppler-based sensor is shown without the other elements of the system, such as the user interface and microprocessor). The sensor generates an electromagnetic beam 174, such as a laser beam, to bounce off the ground 176 (e.g., the ski slope) while the user of the system conducts the activity (e.g., skiing). The electromagnetic beam 174 is reflected off the ground by particles 178 which scatter at least a portion of the energy back to the sensor 172 along approximately the same path. Because the ski 170 is in motion, the returned energy is at a slightly different frequency from the outgoing frequency; hence the Doppler shift, which is a measurable quantity. Note that the sensor 172 must be arranged to generate a beam along the side (or in front or back of) the ski in order to "see" the ground 176.

Figure 12A:
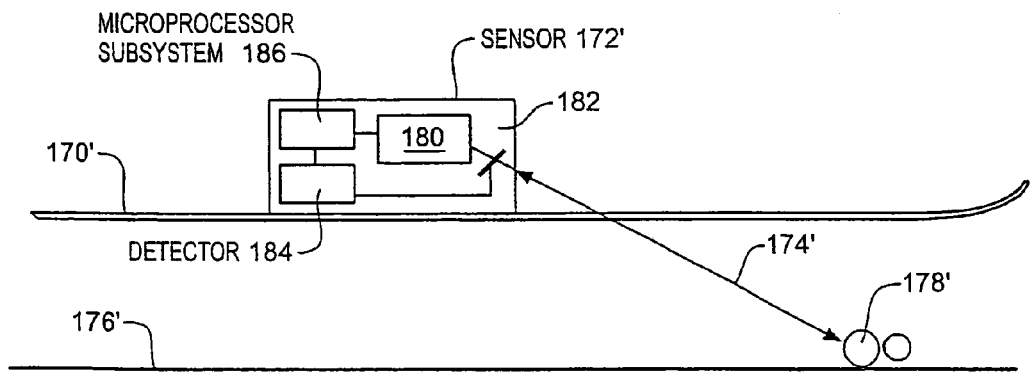
FIG. 12A shows a laser-based Doppler speed sensor constructed according to the invention.

The energy beam 174 is generated in one of two general ways: by a laser diode (to generate a laser beam) or by a piezoelectric transducer (to produce an ultrasonic beam). FIG. 12a, for example, shows a sensor 172' comprising a laser diode 180. The diode 180 generates a laser beam 174' which is reflected by the particles 178' back to the sensor 172'. A small beam-splitting mirror 182 reflects part of the returned beam to a detector 184 which is connected under the overall control of the microprocessor subsystem 186, e.g., the subsystem 12 of FIG. 1 (for illustrative purposes, the other elements of the system of the invention, e.g., the user interface, are not shown in FIG. 12a). The subsystem 186 evaluates the frequency difference between the outgoing beam from the diode 180 and the returned frequency from the detector 184. The frequency difference is readily converted to speed that is displayed on the display, e.g., the display 16 of FIG. 1.

Figure 12B:
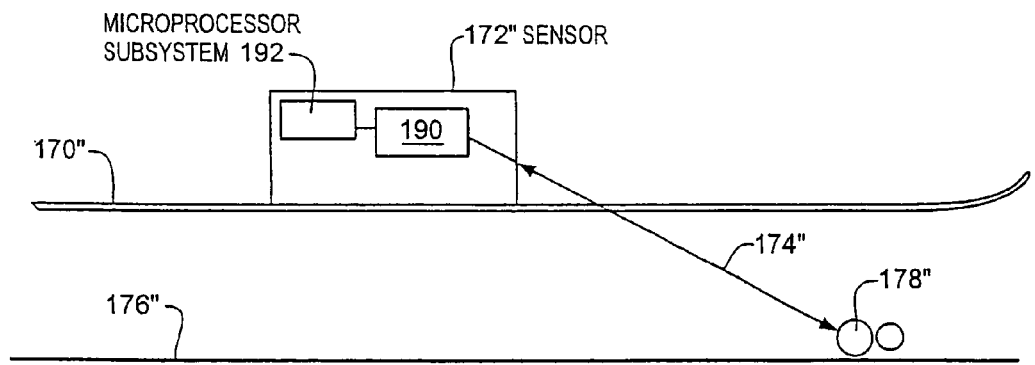
FIG. 12B shows an ultrasonic-based Doppler speed sensor constructed according to the invention.

Likewise, FIG. 12b shows a sensor 172" comprising a piezoelectric transducer 190 which generates an ultrasonic beam 174" that reflects from particles 178" back to the piezo transducer 190, which is connected under the overall control of the microprocessor subsystem 192, e.g., the subsystem 12 of FIG. 1 (for illustrative purposes, the other elements of the system of the invention, e.g., the user interface, are not shown in FIG. 11b). The microprocessor subsystem 192 generates a voltage at a set frequency to drive the piezoelectric transducer 190, to thereby generate the beam 174". The reflected Doppler-shifted beam returns through the transducer 190 (alternatively, through another piezo transducer (not shown)) and generates a voltage at the frequency of the reflected beam. The subsystem 192 evaluates the frequency difference between the outgoing ultrasonic beam 174" and the returned frequency. As above, the frequency difference is readily converted to speed (via a conversion technique that is known to those skilled in the art) that is displayed on the display, e.g., the display 16 of FIG. 1.

Loft Sensor: Accelerometer Based

Modern navigation systems utilize a plurality of accelerometers to determine speed and direction. Particularly complex military systems, for example, utilize three translational and three rotational accelerometers to track direction and speed even during complex angular movements and at extremely high velocities.

In accord with the invention, a similar plurality of accelerometers is used to determine speed. However, unlike military systems, one goal of the invention is to track speeds of sporting vehicles (e.g., a ski) that generally travel in one direction, namely forward. Therefore, the complexity of the accelerometer package is reduced since the orientation of the sensor may be fixed to the vehicle; and fewer than six accelerometers can be used to determine speed.

Accelerometers are well-known to those skilled in the art. They include, for example, translational and rotational accelerometers. FIG. 13 illustrates a speed sensor 200 constructed according to the invention and which includes a plurality of accelerometers 202a-202d. The accelerometers 202a-202d sense various accelerations in their respective axes (accelerometers sense acceleration along a predefined axis, translational or rotational), and each of the outputs from the accelerometers are input to the microprocessor subsystem 204, e.g., the subsystem 12 of FIG. 1, via communication lines 206a-206d. The orientation of the sensitive axis of each accelerometer 202a-202d is stored in the microprocessor subsystem 204 so that a particular acceleration in one axis is properly combined with acceleration values in other axes (as described in more detail below in connection with FIGS. 14 and 14a).

One key point that must be addressed with the accelerometer-based approach: gravity has a huge effect on the accelerometer signals; and gravity must be compensated for in order to achieve reasonable speed accuracy. Therefore, one or more of the accelerometers 202a-202d are used to determine and measure the force or gravity relative to the angle of the vehicle (e.g., the ski) so that gravity may be compensated for by the subsystem 204. Specifically, when the sensor 200 is pointed either downhill or uphill, gravity tends to reduce or increase the measured acceleration output; and that reduction or increase must be adjusted for or else the conversion from acceleration to speed (i.e., the integral of acceleration over time) will be next to useless. Accordingly, the orientations of the accelerometers 202a-202d relative to their respective sensitive axes must be known by the subsystem 204 in order to compensate for the acceleration of gravity, which is generally perpendicular to the motion of the vehicle, but which has a component acceleration in the direction of movement when the vehicle is pointed downwards or upwards.

It should be clear to those skilled in the art that fewer, or greater, numbers of accelerometers are within the scope of the invention, so long as they collectively determine speed. In effect, the fewer number of accelerometers results in reduced accuracy; not reduced functionality. Rather, in an ideal situation, one accelerometer can be used to detect speed; which is the integral of the acceleration over time. Further, a double integration over the same period provides distance; and, therefore, the invention can also provide distance in at least one embodiment of the invention.

It should also be noted that any of the accelerometers 202a-202d of FIG. 13 can be used, in accord with the invention, as the loft sensor 20 of FIG. 1 and without a separate component to measure "air" time. This is because each of the accelerometers 202a-202d generate a spectrum such as described in connection with FIG. 4. Accordingly, one or more of the accelerometers 202a-202d can be used to determine "air" time, described above, without the need for a separate loft sensor.

Figure 14:
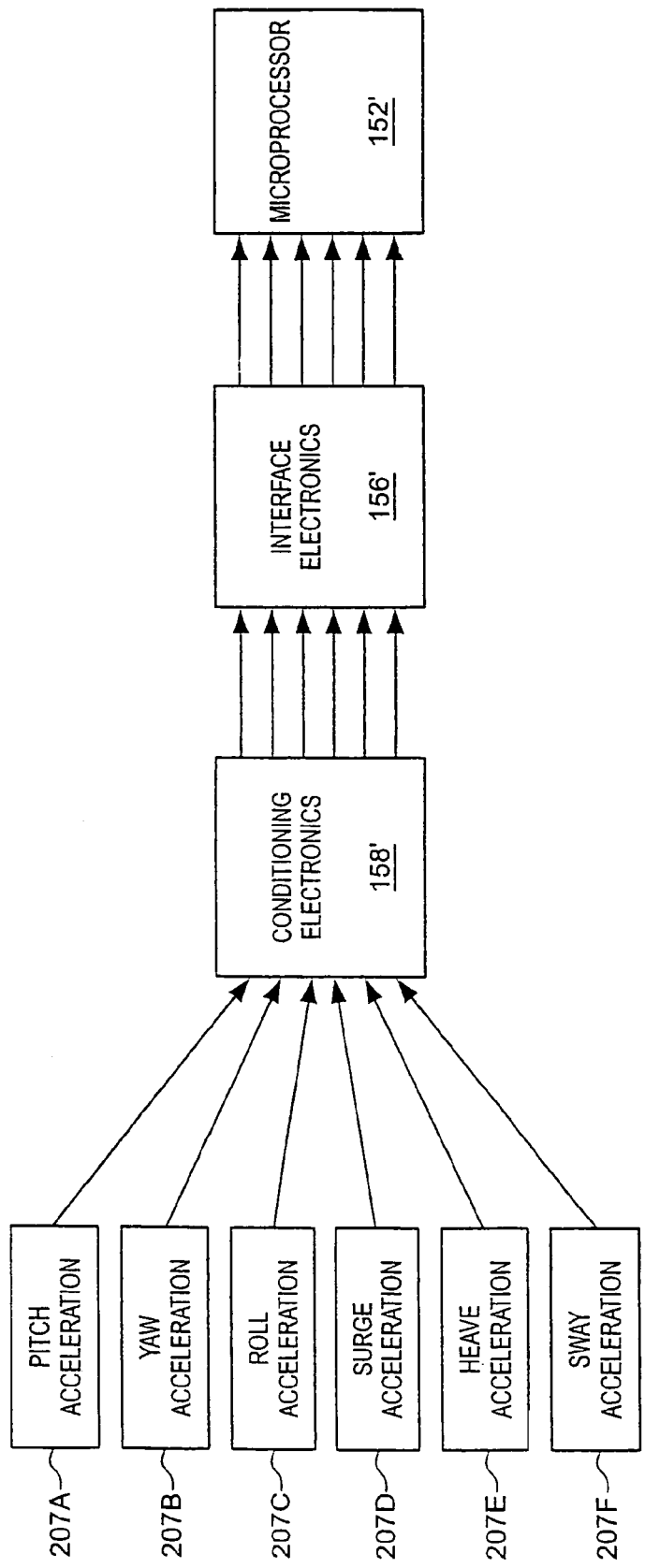
FIG. 14 schematically illustrates process methodology of converting a plurality of acceleration values to speed, in accord with the invention.

FIG. 14 schematically illustrates process methodology, according to the invention, which converts a plurality of acceleration inputs to speed. For example, when a plurality of six accelerometers (e.g., similar to the accelerometers 202a-202d of FIG. 13) are connected to a microprocessor subsystem such as the subsystem 150 of FIG. 10, the process methodology of the invention is preferably shown in FIG. 14. Specifically, six accelerometers are connected with various sensitive orientations to collect pitch 207a, yaw 207b, roll 207c, surge 207d, heave 207e, and sway 207f accelerations. These accelerations are conditioned by the conditioning electronics 158' through the interface electronics 156' and CPU 152' to calculate speed, such as known to those skilled in the art of navigational engineering (for example, *Gyroscopic Theory, Design, and Instrumentation* by Wrigley et al., MIT Press (1969); *Handbook of Measurement and Control* by Herceg et al, Schaevitz Engineering, Pensauker, N.J., Library of Congress 76-24971 (1976); and *Inertial Navigation Systems* by Broxmeyer, McGraw-Hill (1964) describe such calculations and are hereby incorporated herein by reference). The elements 158', 156' and 152' are similar in construction to the elements 158, 156 and 152 described in connection with FIG. 10.

Figure 14A:
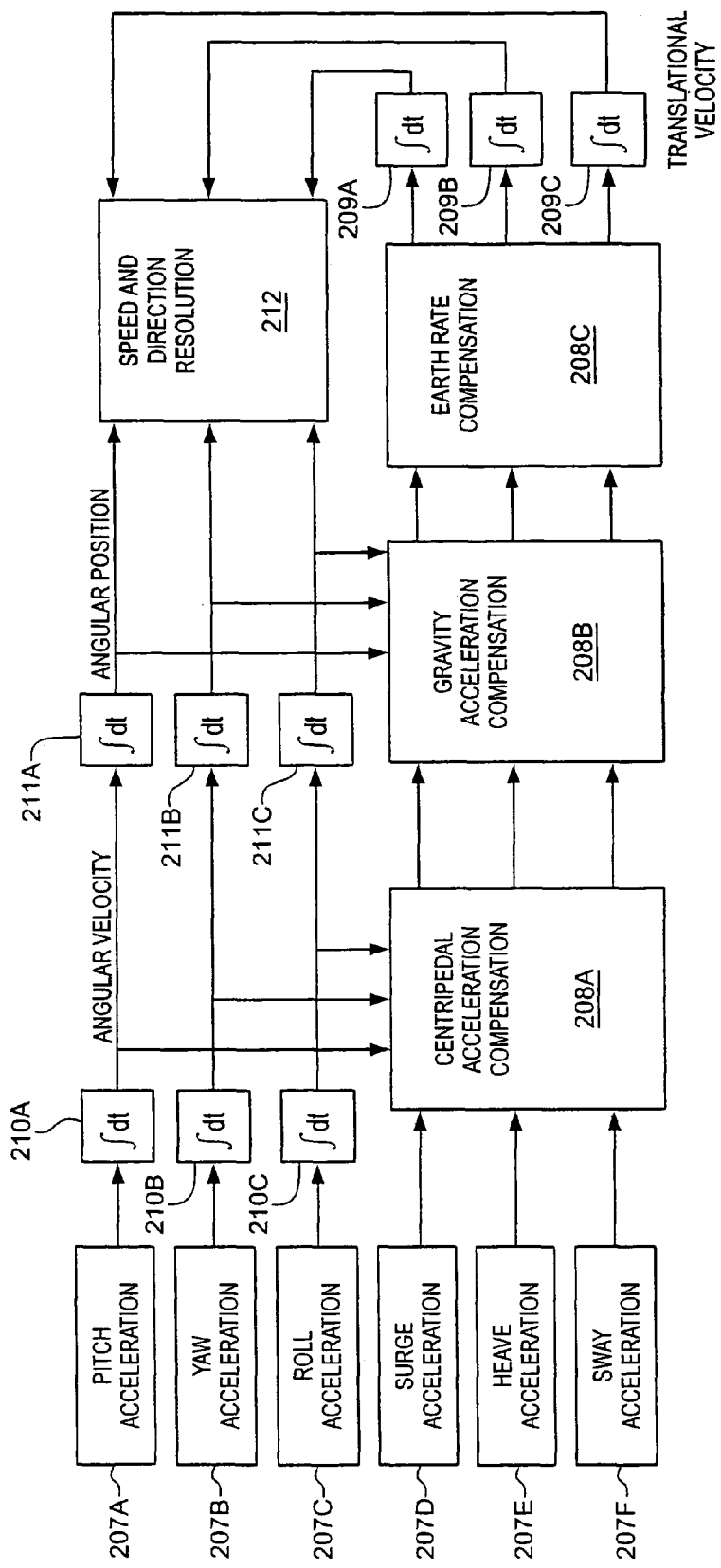
FIG. 14A schematically illustrates a process methodology of calculating speed, direction, and vehicle height, in accord with the invention, by utilizing the accelerometer-based sensors of the invention.

FIG. 14A schematically illustrates further process methodologies according to the invention wherein the six acceleration inputs 207a-207f are processed by the microprocessor subsystem of the invention (e.g., subsystem 12 of FIG. 1) such that centripetal, gravitational, and earth rate compensations are performed so that the various accelerations are properly integrated and compensated to derive speed (and even direction and distance). Specifically, a microprocessor subsystem of the FIG. 14A embodiment includes a centripetal acceleration compensation section 208a which compensates for motions of centripetal accelerations via inputs of surge 207d, heave 207e, and sway 207f. A gravity acceleration compensation section 208b in the subsystem further processes these inputs 207d-207f to compensate for the acceleration of gravity, while a earth rate compensation section 208c thereafter compensates for the accelerations induced by the earth's rotation (e.g., the earth rate acceleration at the equator is approximately opposite in direction to the force of gravity).

Also shown in FIG. 14A are translational integrators 209a-209c which convert the compensated accelerations from inputs 207d-207f to translational velocities by integration. Integrators 210a-210c likewise integrate inputs of pitch 207a, yaw 207b, and roll 207c to angular velocity while integrators 211a-211c provide a further integration to convert the angular velocities to angular position. The angular positional information and translational velocity information is combined and processed at the speed and direction resolution section 212 to derive speed and direction. Preferably, the subsystem with the components 208, 209, 210, 211 and 212 is calibrated prior to use; and such calibration includes a calibration to true North (for a calibration of earth rate).

It should be noted that fewer of the inputs 207a-207f may be used in accord with the invention. For example, certain of the inputs 207a-207f can be removed with the section 208a so that centripetal acceleration is not compensated for. This results in an error in the calculated speed and direction; but this error is probably small so the reduced functionality is worth the space saved by the removed elements. However, with the increased functionality of the several inputs 207a-207f, it is possible to calculate loft height in addition to speed because distance in three axes is known. Therefore, the invention further provides, in one embodiment, information for displaying height achieved during any given "air" time, as described above.

It should be apparent to those in the art that the accelerometers of FIGS. 13-14 provide sufficiently detailed information such that the whole of the system according to the invention can be mounted to a user of the system directly, rather than directly to a vehicle. With the scope of the compensations described in connection with FIG. 14A, for example, movements of the human body, e.g., centripetal motions, may be compensated for to derive speed and/or loft time information that is uncorrupted by the user's movements. Such compensations, however, require powerful processing power.

Seed Sensor: Pressure Based

Figure 15:
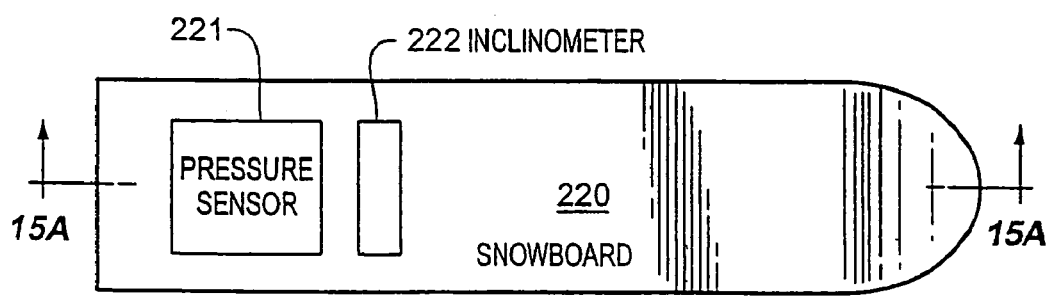
FIGS. 15 and 15A illustrate a pressure-based speed sensor constructed according to the invention.
Figure 15A:
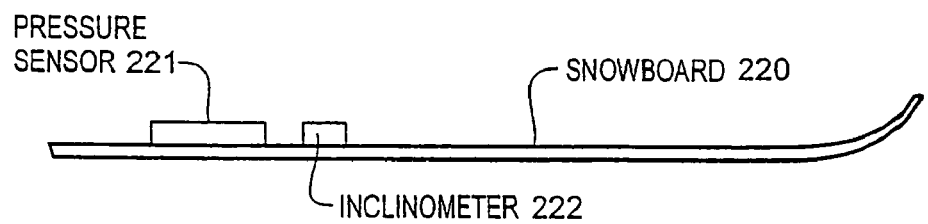

Pressure of the air is used in aviation to determine how high an aircraft is. The higher the altitude the lower the air pressure. Pressure sensors according to the invention convert air pressure to an analog voltage. When mounted to a snowboard 220, such as shown in FIGS. 15 and 15A, the pressure sensor 221 is used to determine the altitude of the snowboarder. This voltage is read by the microprocessor subsystem (e.g., the subsystem 12 of FIG. 1) at a fixed rate and differentiated to determine rate of descent or speed in the vertical direction. This may be converted to speed along the path by knowing the grade or angle of descent. Angle of descent is known by predetermining the geometry of the ski path or by the addition of a inclinometer 222 which gives a voltage dependent upon the angle, with respect to vertical, of the platform. The inclinometer 222 measures zero when the ski is traveling along a level path and the pressure sensor is showing a constant pressure. When the ski moves downhill, for example, the inclinometer 222 measures the angle of descent and the pressure sensor measures ever increasing pressure. Since the angle of descent is known, as is the rate of descent, the true speed is determined and displayed.

Those skilled in the art should understand that the elements 221 and 222 are connected in circuit with the further elements of the invention, e.g., the microprocessor subsystem 12 of FIG. 1; and that elements 221 and 222 are shown in FIG. 15 for illustrative purposes only when in fact they exist integrally with the system of the invention, e.g., the system 10 of FIG. 1.

Speed Sensor: Voltage-Resistance Based

Figure 16:
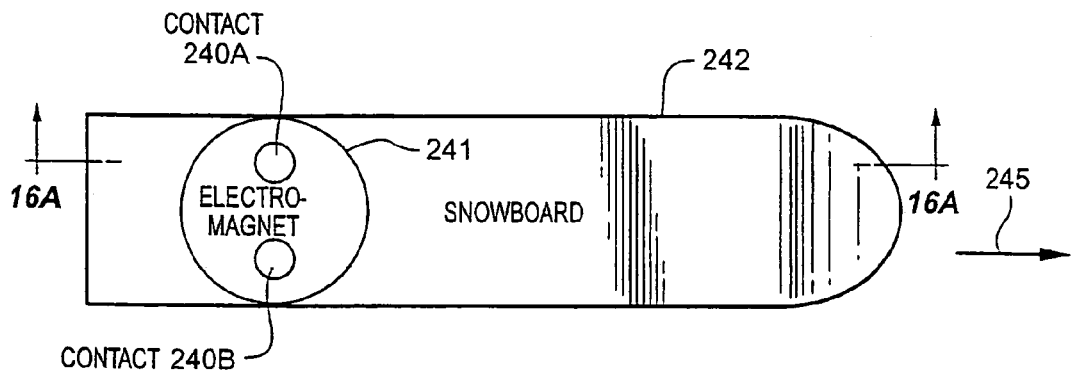
FIGS. 16 and 16A illustrate a magnetic/voltage-based speed sensor constructed according to the invention.
Figure 16A:
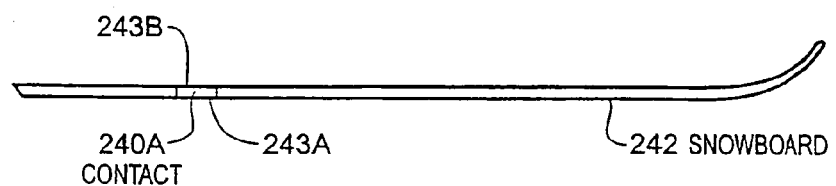

Under-water vehicles and many oceanographic instruments measure water velocity by taking advantage of the principle discovered by Faraday that a conductor moving through a magnetic field produces a voltage across the conductor. The voltage produced is greatest when the conductor is orthogonal to the magnetic field and orthogonal to the direction of motion. This principal is used, in accord with the invention, to determine the speed that a skier moves over the snow in winter skiing or over the water in water skiing. As shown in FIGS. 16 and 16A, an electromagnet 241 is mounted to a snowboard 242. Two contacts 240a, 240b are mounted to the snowboard 242 such that the bottom 243a makes contact with the snow and the top 243b of the contacts are connected to a voltage-measuring circuit within the conditioning electronics (such as the electronics 158 of FIG. 10 and such as known to those skilled in the art). When the snowboard 242 is flat on the snow, a conduction path is set up between the two contacts 240a, 240b and through the snow. When the electromagnet 241 is energized, a magnetic field 244 is imposed on the conduction path. As the snowboard 242 moves in the forward direction 245, the conduction path through the snow moves with the snowboard 242. This represents a moving conductor in a magnetic field; and as Faraday's theorem requires, a voltage 246 across the two terminals 240a, 240b will be generated that is proportional to the snowboarder's speed. This voltage 246 is read by the microprocessor subsystem (e.g., the subsystem 12 of FIG. 1). When the voltage abruptly goes to zero, and thereafter returns to a high voltage, the microprocessor subsystem determines that the gap in voltage is "air" time. Accordingly, in such an embodiment, no separate sensor 20 is required to measure "air" time (such as described above).

Figure 16B:
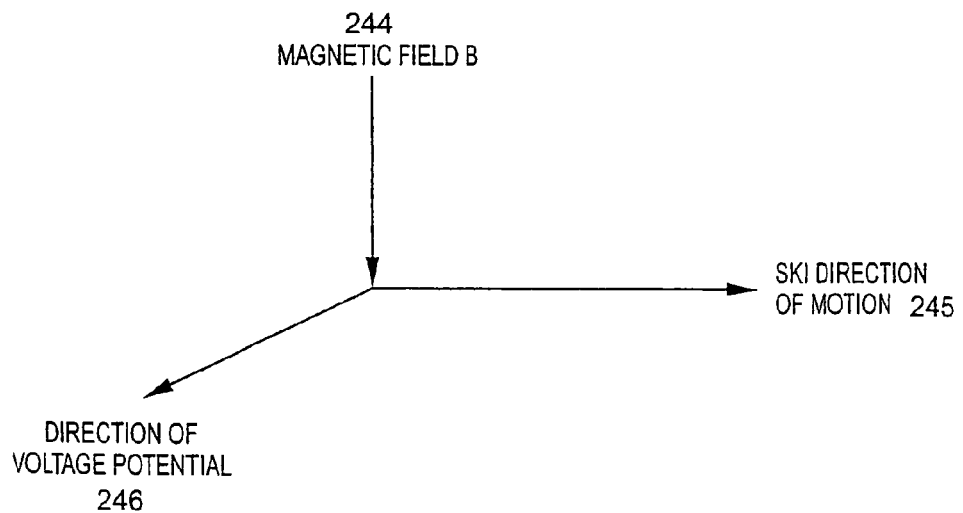
FIG. 16B shows relative motions, magnetic field directions, and voltages associated with the sensor of FIGS. 16 and 16A.

Those skilled in the art will appreciate that the elements of FIGS. 16-16B are shown illustratively for ease of understanding and without the further necessary elements of the invention, e.g., the microprocessor subsystem 12 of FIG. 1.

Figure 17:
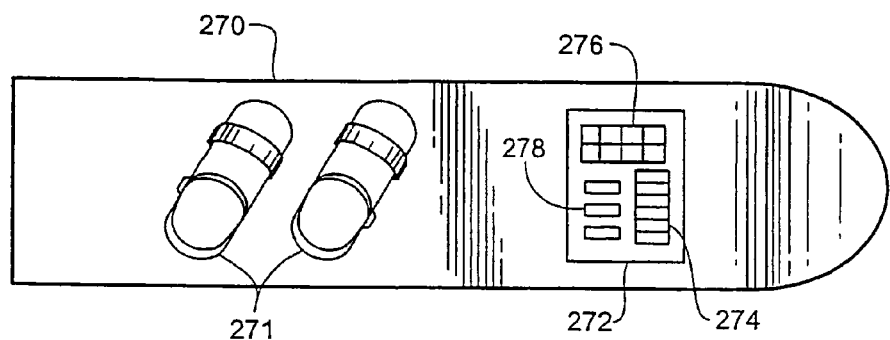
FIG. 17 illustrates an improvement to a snowboard in accord with the invention.

It should be clear to those skilled in the art that certain modifications can be made to the invention as described without departing from the scope of the invention. For example, vehicles other than skis and mountain bikes may be used with the invention. One vehicle, the snowboard, used in the ever popular snowboarding sport, is particularly well-suited for the invention (e.g., there is no jump skiing). The snowboard also has a wide body and a system constructed according to the invention can be incorporated within the body with the user interface, display, and associated buttons at the snowboard surface, for easy access. FIG. 17 shows such an improvement to a snowboard in accord with the invention. Specifically, a snowboard 270, with boot holder 271, incorporates a system 272 constructed according to the invention. The system 272, like the system 10 of FIG. 1, has a display 274, a user interface 276 that provides a user with buttons to selectively access speed and loft time, as described above, and one or more display portions 278 to display identification information about the displayed times (such as described in connection with FIG. 3).

Figure 18:
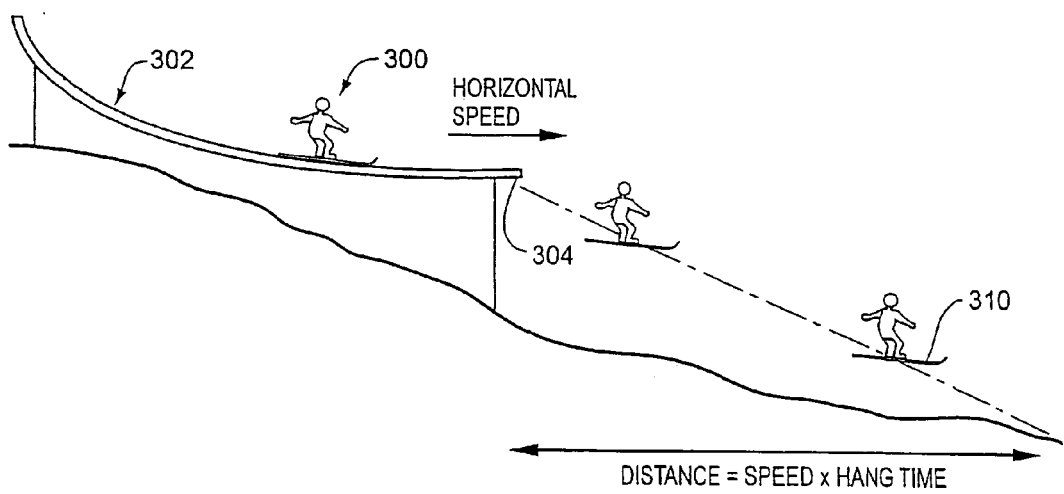
FIG. 18 illustrates one use of the invention for detecting speed, "air," and distance in the sport of ski flying (or ski jumping) in accord with the invention

FIG. 18 shows yet another use of the invention. Specifically, a further application of the invention is found in the sport of ski jumping and ski flying. Ski flying is similar to ski jumping except that ski jumping uses special, extra-long skis, while ski flying uses standard alpine skis. The participant 300 skis down the long ramp 302, which may be as high as twenty-five stories, and launches horizontally into the air at the end 304 of the ramp 302. The objective of the sport is for the participant 300 to "jump" or "fly" through the air for as long as possible, and covering the greatest distance as possible. A system constructed according to the invention (not shown) is attached to the ski 310 to measure "air" time, speed, and distance, as described herein. In particular, the speed at the end 304 is used to predict distance by well-known Newtonian physics so that the participant's overall jump distance is calculated. This removes the necessity of having judges and/or other expensive equipment monitor the event, as the recorded "air" and jump distance is readily displayed by the system of the invention.

It is accordingly intended that all matter contained in the above description or shown in the accompanying drawings be interpreted as illustrative rather than in a limiting sense.

It is also intended that the following claims cover all of the generic and specific features of the invention as described herein, and all statements of the scope of the invention which, as a matter of language, might be said to fall there between.

We claim:

1. An accelerometer based movement monitoring system, comprising:
   a sensor configured to be attached to a person in motion and including at least one accelerometer configured to sense a vibration spectrum of the person relative to the ground; and
   a processor configured to:
      process the vibration spectrum to detect a reduction in the vibration spectrum of the person at a first time period and an increase in the vibration spectrum at a second time period to determine when the person is in contact with the ground while in motion; and
      in response to determining that a duration of time between the first time period and the second time period exceeds a boundary condition, exclude data of the vibration spectrum that occurs during the duration of time.

2. System of claim 1, the processor further being configured to process the vibration spectrum to determine speed of the person.

3. System of claim 2, further comprising a display, that when in operative communication with the processor, is configured to display the speed to the person.

4. System of claim 1, the processor further configured to process the vibration spectrum to determine distance traveled of the person.

5. System of claim 4, further comprising a display, that when in operative communication with the processor, is configured to display the distance traveled.

6. System of claim 5, the display comprising a liquid crystal display configured to be attached to the person.

7. A method of determining one or both of speed and distance traveled of a moving person, comprising:
   sensing one or more accelerations of the person while moving over a surface by a sensor that includes at least one accelerometer;
   sensing a vibration spectrum of the person relative to the surface while moving over the surface;
   detecting, by a processor, a reduction in the vibration spectrum of the person at a first time period and an increase in the vibration spectrum at a second time period;
   determining, from the accelerations and the vibration spectrum, when the person is in contact with the surface and when the person is not in contact with the surface, to determine one or both of speed and distance traveled of the person;
   determining an airtime of the person while in motion, by comparing acceleration signals and the vibration spectrum; and
   in response to determining that a duration of time between the first time period and the second time period exceeds a boundary condition, excluding data of the vibration spectrum that occurs during the duration of time.

8. The method of claim 7, further comprising utilizing a plurality of accelerometers as inertial sensors to sense the one or more accelerations in at least two different axes, and integrating the accelerations over time to calculate one or both of the speed and distance traveled.

9. The method of claim 7, the step of determining comprising compensating for one or more of gravity and centripetal acceleration to determine the speed or the distance traveled.

10. The method of claim 7, further comprising displaying one or both of the speed and distance traveled to the person via a liquid crystal display attached to the person.

11. The system of claim 1, the processor processing the data through state machine logic attached with the person.

12. The system of claim 1, further comprising a state machine for processing the data to determine whether the sensor is coupled with the ground or not.

13. A method of monitoring motion of a sportsman, comprising:
   sensing acceleration of the sportsman by a sensor including at least an accelerometer;
   sensing a vibration spectrum of the sportsman relative to the ground;
   processing, by a processor, the vibration spectrum to detect a reduction in the vibration spectrum at a first time period and an increase in the vibration spectrum at a second time period to determine when the sportsman is in contact with the ground while in motion; and
   in response to determining that a duration of time between the first time period and the second time period exceeds a boundary condition, excluding data of the vibration spectrum that occurs during the duration of time.

14. The method of claim 13, further comprising processing data representative of the acceleration by the processor attached with the sportsman, to determine one or both of speed and distance traveled.

15. The method of claim 14, further comprising generating timing information via a clock attached to the sportsman, to provide timing signals used in determining at least one of the speed and distance traveled.

16. The method of claim 13, the step of sensing acceleration comprising utilizing a plurality of accelerometers attached to the sportsman.

* * * * *